United States Patent
Frederiksen et al.

(10) Patent No.: US 10,015,601 B2
(45) Date of Patent: Jul. 3, 2018

(54) HEARING DEVICE AND MONITORING SYSTEM THEREOF

(71) Applicant: Oticon A/S, Smørum (DK)

(72) Inventors: Lars Pinnerup Frederiksen, Smørum (DK); Thorvaldur Oli Bodvarsson, København (DK); Søren Hesselballe Larsen, Smørum (DK); Lars Bramsløw, Smørum (DK); Niels Søgaard Jensen, Allerød (DK); Filip Marchman Rønne, Smørum (DK); Ariane Laplante-Lévesque, Smørum (DK); Eline Borch Petersen, Smørum (DK); Carina Graversen, Smørum (DK); Lasse Juul Villadsen, Middelfart (DK); Rikke Birksteen Rossing, Smørum (DK); Adis Bjelosevic, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 15/472,621

(22) Filed: Mar. 29, 2017

(65) Prior Publication Data
US 2017/0289704 A1    Oct. 5, 2017

(30) Foreign Application Priority Data
Mar. 30, 2016   (EP) ..................... 16162760

(51) Int. Cl.
*H04R 29/00* (2006.01)
*H04R 25/00* (2006.01)
*A61B 5/00* (2006.01)

(52) U.S. Cl.
CPC ......... *H04R 25/305* (2013.01); *H04R 25/554* (2013.01); *H04R 2225/39* (2013.01); *H04R 2225/55* (2013.01)

(58) Field of Classification Search
CPC .. H04R 2225/55; H04R 25/554; H04R 25/70; H04R 2225/41; H04R 2225/61; H04R 2460/03; H04R 25/305; H04R 2225/39; H04R 25/30; H04R 25/558; H04R 29/00; A61B 5/0002; A61B 5/0022;
(Continued)

(56) References Cited

U.S. PATENT DOCUMENTS

2002/0173991 A1*  11/2002  Avitall .................. G06F 19/327
                                                                      705/2
2003/0138109 A1    7/2003  Bindner et al.
(Continued)

FOREIGN PATENT DOCUMENTS

EP    1 628 503 A2   2/2006
EP    1 628 503 A3   3/2006

*Primary Examiner* — Norman Yu
(74) *Attorney, Agent, or Firm* — Birch, Stewart, Kolasch & Birch, LLP

(57) ABSTRACT

A system for monitoring the status and/or performance of one or more hearing devices is disclosed. The system comprises a number of access points configured to receive wireless signals transmitted by the hearing devices, wherein the access points are connected to a central unit communicatively connected to the Internet/cloud, wherein the system is configured to automatically monitor the status and/or performance of one or more parameter of the one or more hearing devices received by access points, wherein the monitored parameters are accessible from the central unit and/or from a cloud service.

21 Claims, 10 Drawing Sheets

(58) Field of Classification Search
CPC ... A61B 5/0205; A61B 5/0496; A61B 5/6817; A61B 5/12; A61B 2560/0242; A61B 2560/0271; A61B 5/021; A61B 5/024; A61B 5/02427; A61B 5/02438; A61B 5/04845; A61B 5/6803; A61B 5/6814; A61B 5/7203; A61B 5/7405; G06F 19/03
USPC ....... 381/60, 56–58, 67, 312, 315, 328–329; 600/301, 300, 316, 528, 586
See application file for complete search history.

(56) References Cited

U.S. PATENT DOCUMENTS

| | | | |
|---|---|---|---|
| 2008/0081975 A1 | 4/2008 | Agashe et al. | |
| 2008/0154098 A1 | 6/2008 | Morris et al. | |
| 2008/0159547 A1* | 7/2008 | Schuler | G01H 3/14 381/56 |
| 2011/0286615 A1* | 11/2011 | Olodort | H04R 1/1025 381/311 |
| 2013/0343585 A1* | 12/2013 | Bennett | H04R 25/554 381/315 |
| 2015/0366471 A1 | 12/2015 | LeBoeuf et al. | |

* cited by examiner

Fig. 5A)
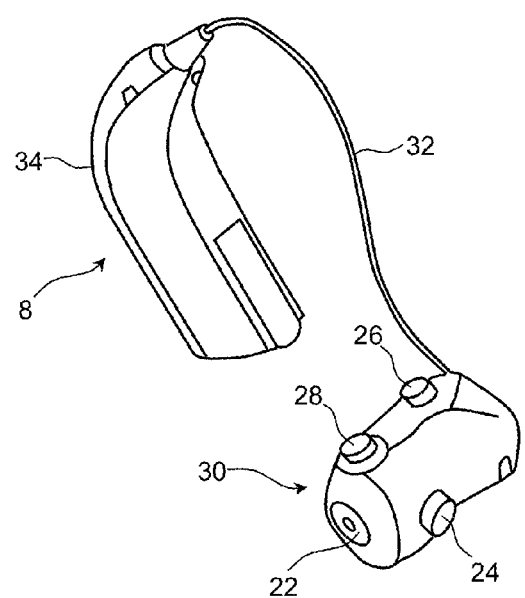
Fig. 5C)
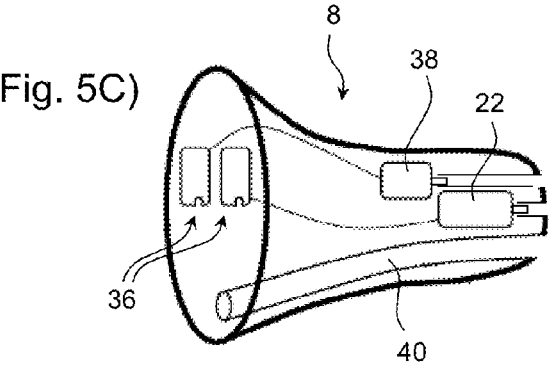
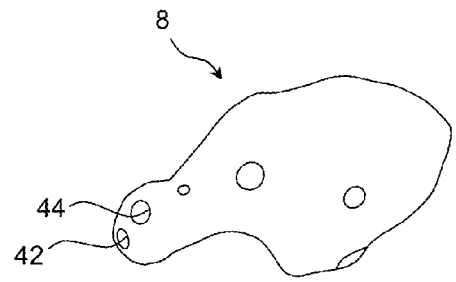
Fig. 5B)

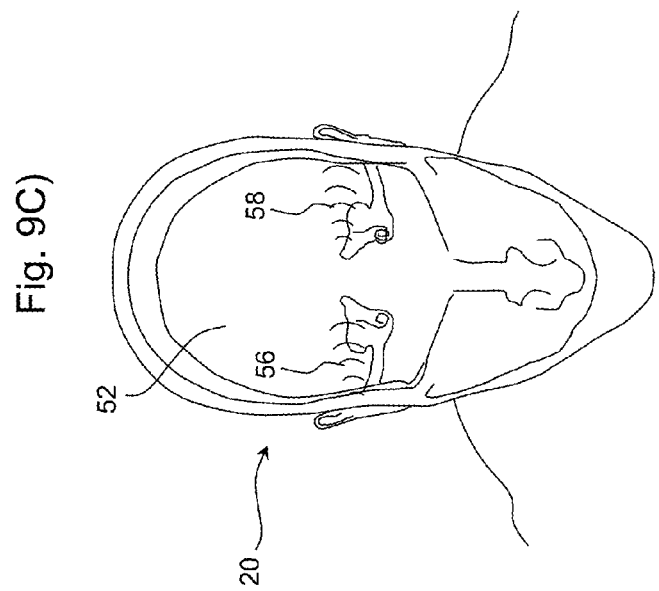
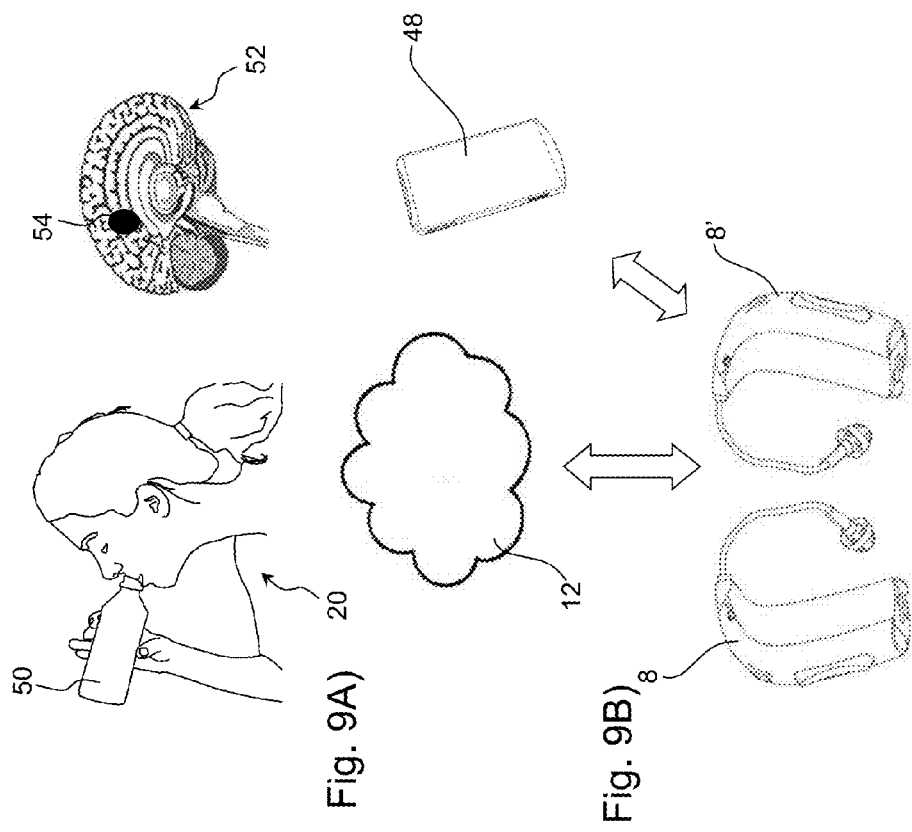

HEARING DEVICE AND MONITORING SYSTEM THEREOF

FIELD

The present disclosure relates to a monitoring system, which is configured to monitor the status and/or performance of one or more hearing devices in an environment. More particularly, the disclosure relates to a system for monitoring health related parameters, wherein the monitored parameters are accessible from a central unit and/or from a cloud service.

BACKGROUND

The increasing focus on health care monitoring and the general perception of having a good life quality in view of the increasing average age amongst humans creates a series of different demands to the health care systems that at least to a degree assists elderly people in maintaining a good quality of life.

With the expansion and developments of the internet and telecommunication possibilities throughout the years the health care system has, started taking advantage of these communications means in order to develop monitoring systems, which may aid a human in obtaining a good quality of life by self-monitoring. Such monitoring systems have been known to e.g. be implemented in auxiliary devices, such as mobile phones, where apps have been developed to monitor different health and performance parameters of a person.

In care taking facilities, usually a series of elderly people are living together and are to a degree dependent on the assistant of caretaking personal for gaining a good quality of life. The caretaking personal are often pressed on time in view of the amount of patients (i.e. elderly people) living in the facility compared to the amount of personnel and resources of the facility. Accordingly, in order to assist the caretaking personal in resource and time optimization, the caretaking personal may benefit from any information that may be collected directly and automatically from the elderly people living in the facility. Furthermore, many elderly people wear health assistant devices, such as hearing aids, which requires maintenance, in the form of battery change, cleaning, dome changing etc. The elderly people wearing e.g. hearing devices often have various levels of mobility, motor skills, mental capabilities and technical awareness. The understanding of e.g. batteries and their limitation, the need of changing them and the ability to do so is not a given capability of all users. Accordingly, the basic maintenance of the instruments and accessories are in caretaking facilities, such as institutions, care centres, old people's homes or hospitals, often the responsibility of caretaking personnel.

In view of the increasing demands on the health care system, and especially the caretaking personal employed in caretaking institutions, there exist a need for a sufficient and high quality monitoring system which allows for a continuously monitoring of residents of e.g. a caretaking facility as well as monitoring of their health assisting devices.

At least an object is to have a desirable, high quality alternative way to ensure the maintenance of auxiliary devices such as hearing devices, while providing for a monitoring of e.g. health parameters of elderly people in a caretaking facility. The present disclosure provides at least a series of suggestions and alternatives on how to monitor one or more hearing aids in an environment, so as to ease the maintenance and monitoring of hearing aid parameters worn by different users in a large environment, where the demand on resources on e.g. the caretaking personal is high.

SUMMARY

According to the disclosure, a monitoring system for monitoring parameters of one or more hearing devices, is provided for. The system comprises one or more hearing devices having one or more sensors configured to perform measurements from said hearing device, and a memory configured to store a set of measurement parameters based on the measurements measured by the sensors. The memory is furthermore configured to store a set of performance parameters of the hearing device. In this way, the hearing device is configured to measure a set of health measurements by use of sensors and to store parameters related to the performance, such as battery status, feedback status, dome position and so forth of the hearing device.

The hearing device is furthermore configured to transmit the stored performance and/or measurement parameter through a wireless signal, wherein the monitoring furthermore comprises a number of access points configured to receive the transmitted stored performance and/or measurement parameters through said wireless signal wherein the number of access points furthermore are configured to transmit the received performance and/or measurement parameters to a central unit, which central unit is configured to communicate with an Internet and/or a cloud service, which enables the measured performance and/or measurement parameters to be shared between a facility having the access points and the central unit and a remotely located facility, such as e.g. a hospital and/or an health clinic.

The central unit according to the monitoring system comprises a processing unit having a set of stored normal values representing each of the one or more measurements and/or performance parameters, and the processing unit is configured to evaluate the received performance and/or measurement parameters against the set of stored normal values in to detect a deviation from the normal value, wherein when a deviation is detected, the processing unit triggers the central unit to prompt an alarm to a user of the monitoring system and/or to transmit a notification signal directly to the hearing device.

With such a monitoring system as defined herein, the caretaking personnel of a health care institution, such as hospitals, elderly home, nursery etc. is able to monitor a series of measured performance and/or sensor measurement parameters collected by a number of hearing device, without having to physically monitor the user of the hearing devices before it is relevant. In this way, the control unit collects measurements and enables the caretaking personal to optimize time and resources in view of maintenances, health monitoring etc. used for assisting humans in gaining a better life quality. That is, the monitoring system informs the caretaking personnel about deviations arising in a hearing device users measurements allowing the personnel to take action when it is relevant. In this way, unnecessary actions are avoided, while at the same time, the necessary actions for assisting the elderly people during the needed times are enabled through this system.

With the control unit receiving, storing and evaluating the one or more measured performance and/or measurement parameters by communication with a series of access points in a facility, changes in e.g. measured health related issues (i.e. measured by the sensors) and/or performance changes of e.g. a hearing device may be monitored for each person wearing a hearing device in the facility at one unit.

Furthermore, with the monitoring system it is possible to provide a system by which it is possible to ensure that the maintenance of hearing devices and their accessories is carried out as scheduled. That is, the status and/or different parameters, for example measured by one or more hearing devices, are communicated to a series of access points of the system. The access points communicatively transmit data of the current status of the hearing device to at least a central unit and/or a cloud based solution, whereby the status may be monitored, checked and/or changed by for example a hearing care professional or any other health care professional, which has access to the data. This could for example be the caring professionals in an elderly home, which with the system according to the disclosure, would be able to monitor, check and/or change the behaviour of the elderly resident hearing aids, or monitor the health parameters measured by the hearing aid.

The performance and/or measurement parameters of one or more hearing devices may include any desirable parameter including the status and/or performance of one or more parameters that can be measured by the hearing devices. Accordingly, such parameters may include measurements made by the hearing device(s) by means of one or more sensors. The one or more sensors may be arranged at least in connection with the hearing devices, such as for example being an integrated part of the hearing device and/or being in communication with one or more sensors placed on a body part of a user.

Such sensors could for example include electrodes, health sensors, skin sensors, accelerometers, antennas or any other kind of suitable sensors for monitoring different health parameters of a person.

The monitoring system comprises a number of access points configured to receive wireless signals transmitted by the hearing devices. The access points may be located in any suitable location in an environment in which a hearing aid user is situated. The access points may be provided as permanent installations in e.g. a health care institution as previously described.

The access points may preferably be connected to a central unit communicatively connected to the Internet/cloud. This may be achieved by means of wireless and/or wired connections. In this way, the data received by the access points may be stored in a cloud solution and/or on the internet, such that a remote access to the data may be achieved. This provides for the possibility of having a remote monitoring of the hearing device, such that for example a doctor or other hearing care professional is able to gain access to the data sent by the hearing devices. The data sent by the hearing device would thus lead to the possibility of a remote health monitoring of the person wearing the hearing device, and thereby aiding a care professional in diagnosing and controlling potential treatment of the hearing device wearer.

Access points may, due to their small size, be placed in public transportation, at strategic locations in the public domain including cultural venues, shopping malls, sport facilities, community centres and religious sites. Accordingly, the system according to the disclosure can provide a service in which hearing care professionals can help their customers remotely while the hearing device users are at home or moving about on their own. The access point may similarly be placed in a nursing home, whereby the care professional of the nursing home would be able to monitor the health status and/or the status of the different hearing devices through the central unit, which receives data from each of the hearing devices worn by a resident of the nursing home.

In an embodiment, the transmitted performance and/or measurement parameters are communicated to the central unit through at least two access points. That is, the data (i.e. the performance and/or measurement parameters) is transferred through at least two access points prior to reaching the central unit. In this way, the access points forms a mesh network, which makes the infrastructure highly scalable, because not all access points are required to be physically connected directly to the network master (i.e. the central unit). Instead, access points can connect directly with other access points within their range, and relay any message, information, status, measured parameters etc. to other access points so that it eventually is delivered from the hearing device to the network master, such as the central unit. In addition, the hearing devices themselves may be applied as access points, and relay information from another hearing instrument to a dedicated access point if it is without connection to a dedicated access point itself. In this way the data transfer is reliably secured, such that if any access points in the mesh is not available, the data may still be transferred in a secure and reliable manner to the central unit, thereby maintaining the monitoring flow to the caretaking personnel.

The monitoring system is configured to automatically monitor measured and/or performance parameters of the one or more hearing devices received by access points and transferred to the central unit.

When transmitted to the central unit, the performance and/or measurement parameters comprises an identification parameter, wherein the central unit is configured to receive the identification parameter and correlate the received identification parameter with a set of identification parameters stored in the central unit, so as to identify the hearing device of said transmitted parameters. In this way, an identification parameter belonging to a resident of the health care facility may be used to store the measured parameters, such as health related parameters to the correct resident. That is, the central unit may contain a database with identification parameters belonging to each of the residence, whereby the central unit is configured to store the incoming measurements from the hearing devices to the correct residents. In this way the central unit automatically stores the data transmitted trough the access point from the hearing devices.

The monitored parameters are accessible from the central unit and/or from a cloud service by means of any suitable communication connection and communication devices. That is, the monitored data could be accessed through a computer, a phone, such as an iphone, an app or any other suitable device at the health care institution and/or remotely from there.

Furthermore, in an embodiment, the number of access points is configured to request a status from one or more hearing devices upon instructions transmitted from said central unit and/or in a continuous, e.g. scheduled manner. In this way it is ensured that the monitoring system continuously request data from the hearing devices of residents in the facility, whereby it is ensured that the caretaking personnel may always follow the status and any change to the parameters, which they should be aware of. Within the meaning of scheduled manner, should be understood, that the access point maybe be configured to request a status in accordance with a given schedule, such as e.g. 3 times a day at certain times, etc.

In a further embodiment, the hearing devices may continuously transmit performance and/or measurement parameters to said access points, wherein said access point is configured to store said performance and/or measurement parameter, such that upon request from said central unit, said performance and/or measurement parameters are transmitted to said central unit. In this way, the central unit may store the parameters upon request, for example, when instructed by a caretaking personnel or in schedule manner as previously described.

According to the disclosure, the monitoring system is configured as a service platform configured to be installed in a care center environment, such as in a nursery, care centers and/or old people home, where the performance and/or measurement parameters may be monitored for several hearing devices at the same time through the central unit in a structured manner. This makes it possible to reduce the resources needed to plan, control and execute an appropriate level of service and maintenance. The service platform may be based on any suitable communication technology, including "Bluetooth low energy" and hearing devices configured to communicate by using "Bluetooth low energy"

Accordingly, in an embodiment, the monitoring system may be configured such that the control unit upon a detected deviation in the transmitted one or more parameters of the one or more hearing device is configured to automatically notify an external device, preferably an external device of service personnel and/or a health professional.

It should be noted that in a preferred embodiment, the number of access points are configured as a plurality of communication devices comprising a battery electrically connected to a printed circuit board having an integrated transmitter unit comprising a radio unit or an antenna for transmission of wireless radio signals, and wherein the plurality of communication devices are installed in e.g. a nursery, care centers and/old people's home.

The one or more access points may comprise a memory for storing the transmitted performance and/or measurement parameters, until a request from the central unit is received.

As already implied the monitoring system is thus configured to monitor a series of different parameters of a hearing device. That is, the monitoring system may be configured to monitor one or more measurement parameters transmitted by the one or more hearing devices and including stored measurements of one or more of: a blood sugar value, a heart rate, a temperature, an acceleration, a vibration, a blood pressure, a skin conductance, an ultraviolet light exposure, a pH level, a bacteria level, a humidity and/or an electrical activity of the brain of the hearing device user(s), wherein the performance parameters may include one or more of a registration of: a battery status of the hearing devices and/or a surroundings and/or a positioning.

Accordingly, a series of different applications of the system exists, which will be explained in more detail in relation to the figures.

An example with regards to the performance parameters of the hearing devices includes that the system according to the disclosure may be configured to monitor the battery level remotely and report low power level to the service provider, such as a nurse, care personnel, a hearing care professional, a doctor, etc. Accordingly, battery change/replacement can be carried out in a scheduled manner by the service provider so that less hearing device 'downtime' is experienced.

By applying a system according to the disclosure, it is possible to extend the battery lifetime by remotely controlling the power scheduling.

By applying a system according to the disclosure, it is also possible to reduce the risk of injury for hearing device users with dementia due to the system's capability of detecting hearing devices leaving a building.

Location-based or situation-based hearing device program choices can be pushed to the hearing device(s). Hereby, by applying a system according to the disclosure, it is possible to give relevant information related to locations or situations to the hearing device users. It is possible to select any desired location, including locations as a TV lounge, a diner room, a movie theatre and relate such location to a predefined information and/or program role.

From the caretaker's/service provider's perspective, the system according to the disclosure solves several problems/challenges:

The system makes it possible to shift from status polling of several hearing device users to a centralised, pushed status from the service platform.

The system makes it possible to gather knowledge of battery level in all hearing devices of the system.

The system makes it possible to report hearing device status of all hearing devices of the system to the service provider.

The system makes it possible to shift from user interrupt based service to proactively planned and executed service.

The system makes it possible to detect the location of the hearing devices and thus the location of the users wearing the hearing devices. This is a valuable tool in situations where users (e.g. with dementia) get "lost".

The system makes it possible to broadcast voice messages or other types of notifications to the hearing device users when needed.

It may be an advantage that the system according to the disclosure is configured to monitor the hearing device status and notify service personnel in a nursing home or another relevant institution or building. It is preferred that the system according to the disclosure comprises a plurality of access points that are connected to a central unit.

It may be beneficial that the system according to the disclosure comprises a plurality of access points arranged strategically around the property in such a manner that the access points are capable of monitoring the status of the hearing devices located within the range of each access point.

It may be an advantage that the access points are configured to request the status from the individual hearing device. This could for example be done in a scheduled manner, such that data from the hearing devices are collected for example in the evening, during sleep. The data may however also be sent to the access point continuously during the day, while worn by the hearing device, e.g. hearing aid user.

The system according to the disclosure may be configured to generate an alert in case that a hearing device user leaves a predefined area.

By way of example, if a demented hearing impaired patient at a nursing home leaves the institution without informing the personal, the system will detect that the hearing device user leaves the predefined area within the nursing home. The system informs the personnel so that they can react preventively.

The system according to the disclosure is configured to detect when the battery in the user's hearing device is approaching a critical, low level. The system informs the personnel in advance so that they can schedule the replacement of the user's battery into their daily routine, thus preventing unwanted dysfunctional hearing aid due to power loss. The system may similarly be configured to push a notification message to the hearing aid user that the battery is low, and providing sound instructions to change the battery.

The system according to the disclosure may be configured to detect when a hearing device user has lost the hearing device. Accordingly, by using triangulation or other relevant technology, the lost hearing device can be found again. For this purpose, sensors detecting for example adjacent skin heat or other suitable measures could be used to detect the placement or non-placement of the hearing aid on the ear of a user.

According to the disclosure, the system may also comprise a plurality of access points communicatively connected to the central unit.

Hereby, it is possible to provide a system that covers a large area and to detect the position of hearing devices all over the area.

According to the disclosure, the access points may be permanent installations, preferably permanent installations in and/or in close proximity of a building.

Hereby, it is possible to apply the fixed position of the access points to determine the position of the hearing devices. Moreover, it is possible to provide the access points with power through the mains.

Furthermore, according to the disclosure, the access points may be configured to be a movable/portable device. Hereby, it is possible to build up a system or increase the size of a system with movably/portable access points in case that a larger area is required to be covered or if the location of the access points is required to be changed frequently.

In addition, according to the disclosure, the signals transmitted by the hearing devices may include information of battery status of the hearing devices and/or the blood sugar value, and/or the heart rate and/or the temperature and/or the acceleration and/or the vibration and/or position and/or the blood pressure and/or the skin conductance and/or the ultraviolet light exposure and/or the pH level and/or the bacteria level and/or the humidity and/or the electrical activity of the brain of the hearing device user(s) and/or the surroundings.

Hereby, it is possible to apply the system according to the disclosure for a large range of purposes including health monitoring. This would especially be suitable for monitoring diseases, scheduling medicine intake, storing health data for a doctor to evaluate further and so forth.

In an embodiment of the disclosure, the system is configured to detect the location of the hearing device user by using triangulation between two or more, such as three access points.

According to a further embodiment of the disclosure, the system is configured to automatically notify an external device, preferably an external device of a service personal and/or a health professional. Hereby, the system is capable of being used to generate alerts or provide useful information to relevant personnel.

According to yet another embodiment of the disclosure, the system is configured to generate an alert and/or notify an external device based on a predefined calendar event (e.g. a specific date and time).

Hereby, predefined calendar events e.g. in a smartphone may be used to generate alerts or notifications.

According to another embodiment of the disclosure, the system is configured to generate an alert and/or notify an external device, preferably an external device of a service personal and/or a health professional, in case that the detected position of a hearing device user is outside a predefined range/area of positions.

Hereby, the system according to the disclosure can be used to keep track of hearing device users e.g. hearing device users that are not allowed to leave a predefined area.

According to a further development of the disclosure, the system is configured to send one or more notifications to one or more of the hearing device users.

Hereby, it is possible to use the system according to the disclosure to inform and/or instruct the hearing device user about relevant information and/or tasks when required. This could for example be to change the battery, intake of medicine, high or low level of blood sugar, temperature indicated illness or any other suitable measure.

According to a further aspect according to the disclosure, the system is configured to:
A) automatically generate and send a notification to one or more of the hearing device users when one or more of the parameters of the one or more hearing devices are outside a predefined range and/or
B) receive an instruction from an external device, preferably an external device of a service personal and/or a health professional, and generate and send a notification to one or more of the hearing device users based on the received instruction.

Hereby, the system according to the disclosure can be used to treat hearing device users remotely e.g. by health professionals including physicians.

According to the disclosure, the one or more notifications may be implemented as voice messages pushed to the hearing device of interest.

Hereby, it is possible to provide the hearing device users with information in an easy manner. The receiver of the hearing devices may be used to generate the voice messages.

According to an embodiment of the disclosure, the one or more notifications is a voice message instructing the hearing device users to ingest fluid (e.g. water) and/or medicine.

Hereby, the system can be used to prevent dehydration and a patient forgetting to take a medication.

According to another embodiment of the disclosure, the one or more notifications received by the hearing device users are generated on the basis of detection of water level in the brain of the hearing device users and/or the bio impedance of the hearing device users and/or the glucose level of the hearing device users.

Hereby, the system according to the disclosure can be used to prevent dehydration and a critical glucose level of the hearing device users.

Furthermore, according to the disclosure, the system is configured to carry out measurements of the electrical activity of the brain of a hearing device user by using one or more hearing devices provided with sensors for detection of the electrical activity of the brain of a hearing device user.

Hereby, the system according to the disclosure can be used to estimate the overall mental energy of the wearer of the hearing device.

In addition, the system may be configured to detect the acceleration of one or more of the hearing devices by using one or more hearing devices provided with sensors for detection of the acceleration of a hearing device user.

Hereby, the system according to the disclosure may be used to detect if the hearing device user is falling or moving (e.g. doing sport).

Another implementation according to the disclosure is for the system to detect the heart rate of one or more of the hearing device users by using one or more hearing devices provided with sensors for detection of the heart rate of a hearing device user.

Hereby, the system according to the disclosure may use the heart rate to process the signals according to predefined roles dependent on the heart rate. Moreover, the system may be used as a health monitoring tool.

According to an embodiment of the disclosure, the system may be configured to detect the temperature of one or more of the hearing device users by using one or more hearing devices provided with sensors for detection of the temperature of a hearing device user. Hereby, the system according to the disclosure may be used as a health monitoring tool that includes temperature measurements.

According to another embodiment of the disclosure, the system is configured to detect the temperature of one or more of the hearing devices at one or more predefined times. Hereby, the system can detect when the temperature of the hearing device user changes over time (which may indicate sickness).

Furthermore, the system may be configured to detect the user patterns on the basis of the temperatures.

Hereby, the system may set the processing settings on the basis of detected temperatures (e.g. sports setting when the body temperature increases due to physical activity).

In addition, the system may be configured to detect the blood glucose level of one or more of the hearing device users by using one or more hearing devices provided with sensors for detection of the blood glucose level of a hearing device user.

Hereby, the user may be informed in case that an insulin dose is required.

According to a further embodiment, the system is configured to detect the water level in the brain of one or more of the hearing device users by using one or more hearing devices provided with sensors for detection of the water level in the brain.

Hereby, it is possible to prevent illness in the brain by using a system according to the disclosure.

The system may also, according to the disclosure, be configured to detect the degree of dehydration and/or the humidity and/or the bio impedance of one or more of the hearing devices users by using one or more hearing devices provided with one or more sensors for detection of the degree of dehydration and/or humidity and/or bio impedance of a hearing device user.

Hereby, the system according to the disclosure may be used to prevent dehydration of the hearing device user.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effects will be apparent from and elucidated with reference to the illustrations described hereinafter in which:

FIG. 5A shows a schematic perspective view of a hearing device according to an embodiment of the disclosure provided with sensors;

FIG. 5B shows a schematic perspective view of another hearing device according to an embodiment of the disclosure;

FIG. 5C shows a schematic perspective view of a further hearing device according to an embodiment of the disclosure;

FIG. 9A shows a schematic view of a hearing device user drinking in response to a thirst signal;

FIG. 9B shows a schematic view of a left and right hearing device communicating with a smartphone 8 and via the Internet;

FIG. 9C shows a hearing device user 20 wearing a first hearing device and a second hearing device and FIG. 10 shows a first hearing device user (a baby) and a second hearing device user (a child) using wearable health monitoring hearing devices.

DETAILED DESCRIPTION

Figure 1:
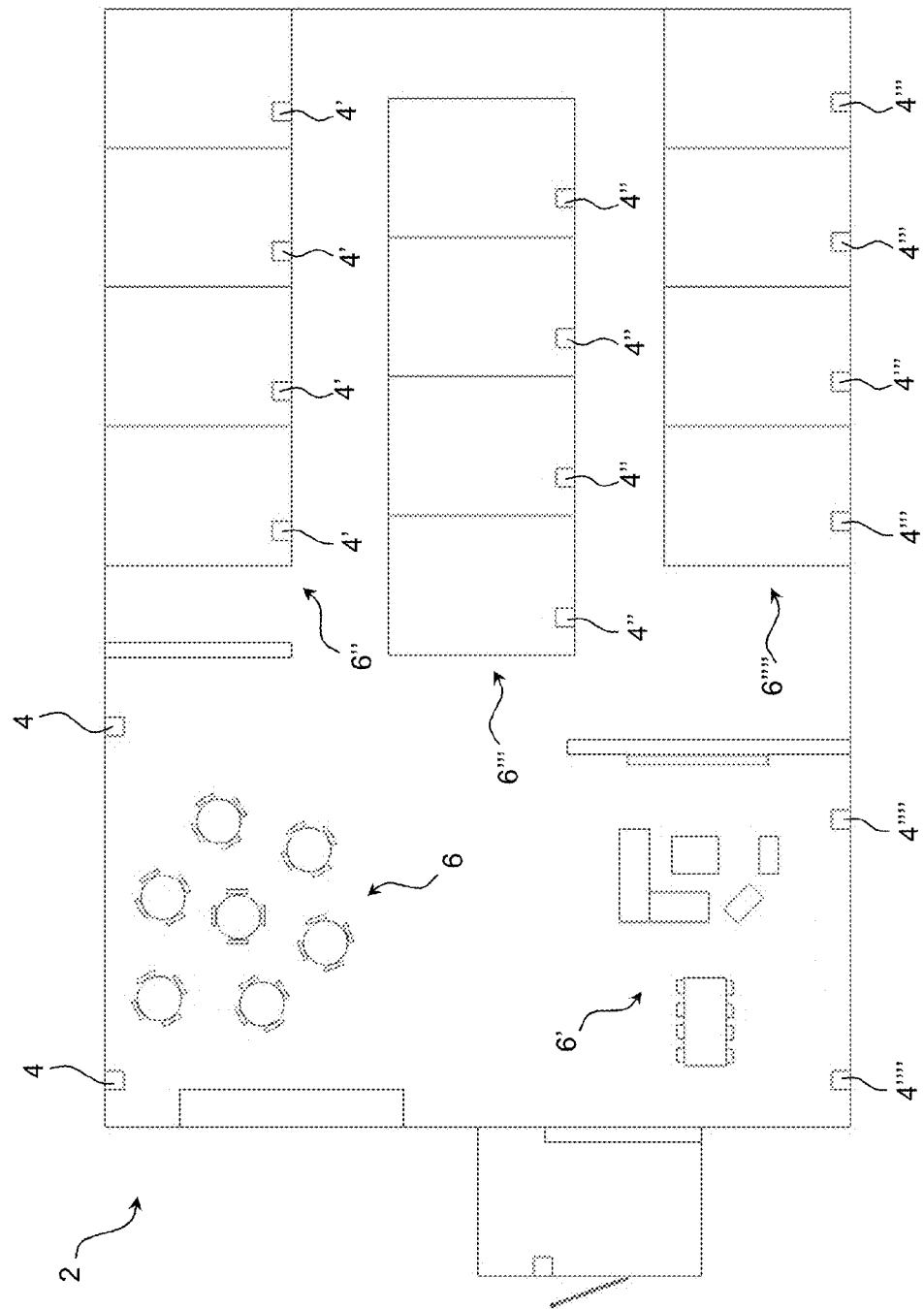
FIG. 1 shows a schematic view of a system according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several embodiments of the apparatus and system are described by various blocks, functional units, modules, components, circuits, steps, processes, algorithms, etc. (collectively referred to as "elements"). Depending upon particular application, design constraints or other reasons, these elements may be implemented using electronic hardware, computer programs, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears.

The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicate with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of the following: remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such a directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be noted that any type of hearing aid type, comprising at least some of the above-mentioned features may be used in connection with the system according to this disclosure.

Now referring to FIG. 1, which illustrates a schematic view of a monitoring system 2 according to the disclosure, it can be seen that the monitoring system 2 (also referred to as the system) comprises a plurality of access points 4, 4', 4", 4''', 4'''' provided in different locations 6, 6', 6", 6''' in a building.

The building comprises a dining room (provided with tables and chairs) indicated as a first location 6. Several access points 4 are provided in the first location (dining room) 6. The building moreover comprises a TV room indicated as a second location 6'. A plurality of access points 4'''' are provided in the second location 6'. The building additionally comprises a first residential area indicated as a third location 6", a second residential area indicated as a fourth location 6''' and a third residential area indicated as a fifth location 6''''. A plurality of access points 4', 4", 4''' are provided in the first residential area 6", the second residential area 6''' and the third residential area 6'''', respectively.

The building may be any type of building including an institution, a care center, an old people's home or a hospital.

The access points 4, 4', 4", 4''', 4'''' is preferably a wireless personal area network based on for example bluetooth, such as Bluetooth low energy (Bluetooth Smart) technology. The access points 4, 4', 4", 4''', 4'''' are configured to communicate wirelessly with one or more hearing devices, such as hearing aids. Hereby, the hearing aids of one or more hearing aid users may receive information from the access points 4, 4', 4", 4''', 4'''' and transmit data which is received by the access points 4, 4', 4", 4''', 4''''.

The system is suitable for use in connection with hearing aid users in public as well as private buildings. The system is suitable for being installed in buildings with multiple hearing device users. The data that is collected by means of the access points 4, 4', 4", 4''', 4'''' may be reached by remote individuals including hearing care professionals outside the building. Also it is possibly that the data is stored in a central unit at the location of installation of the access points.

The access points may be provided as small sized communication devices comprising a battery electrically connected to a printed circuit board having an integrated transmitter unit comprising a radio unit and an antenna for transmission of wireless radio signals. Due to their small size, the access points 4, 4', 4", 4''', 4'''' may be placed in public transportation, at various locations in the public domain e.g. in cultural venues, shopping malls, sport facilities, community centers, religious sites.

The plurality of access points 4, 4', 4", 4''', 4'''' constitute a mesh network which is highly scalable because the access points 4, 4', 4", 4''', 4'''' are not required to be physically connected directly to the network master unit. The access points 4, 4', 4", 4''', 4'''' can connect directly with other access points 4, 4', 4", 4''', 4'''' within their range, and relay any message, information or status to other access points 4, 4', 4", 4''', 4'''' in such a manner that it eventually is delivered from a hearing device to the network master unit. In addition, it is possible to apply hearing aids that are configured to be used as access points 4, 4', 4", 4''', 4'''' and relay information received (e.g. from another hearing device) to a dedicated access point 4, 4', 4", 4''', 4''''. One of the access points 4, 4', 4", 4''', 4'''' may function as a network master unit configured to communicate with a remote unit. Such a remote unit may be a server allowing external individuals including hearing care professionals to access the remote unit in order to receive data/information from the hearing devices. Such data/information may include the status of a hearing device including the battery level or power level of the hearing device monitored remotely and reported to the remote unit that may be controlled by a service provider. The data/information may include information related to battery change (battery change may be scheduled and carried out by the service provider). Such feature may reduce the "downtime" of a hearing device and the battery lifetime can be extended by remotely controlled power scheduling.

Generally, the hearing aid status and performance may be monitored and problems may be reported to the remote unit and/or the service provider. The hearing aid status may include the position of the hearing device with respect to the ear canal (so that a wrong positioning of a hearing device can be detected and reported to the remote unit and/or the service provider).

The hearing device status may include the location of the hearing device and thus the location of the hearing device user. In this manner, it is possible to track hearing device users and prevent demented hearing device users from leaving a building. Accordingly, the risk of injury for demented hearing devices can be reduced.

The location of the hearing device and thus the location of the hearing device user may be used to control/regulate the hearing device program being used.

In this manner, it is possible to detect when the hearing device user is in a first location (the dining room) 6 and apply predefined hearing device settings in order to meet the conditions of the first location (the dining room) 6. In the same manner, the system makes it possible to detect when the hearing device user is in another location and apply predefined hearing device settings in order to meet the conditions of this other location. It is possible to use the time to further fine-tune the settings. In this manner, the system according to the disclosure may apply information about both the location of the hearing device user and the time to provide the most optimum settings. If the hearing device user is located in the dining room about dinnertime, dinnertime specific settings may be applied. Likewise, the system may be configured to apply predefined hearing device settings dependent on other locations It is possible to apply various health monitoring features (e.g. heart rate, blood pressure or temperature) which may provide the hearing aid user with a sense of security when wearing the hearing device.

The system according to the disclosure makes it possible for the caretakers/service provider to have access to data from a plurality of users in the same the remote unit (e.g. a server) using only one platform. It is in particular possible for the caretakers/service provider to gain precise knowledge of battery level in all hearing devices.

Figure 2:
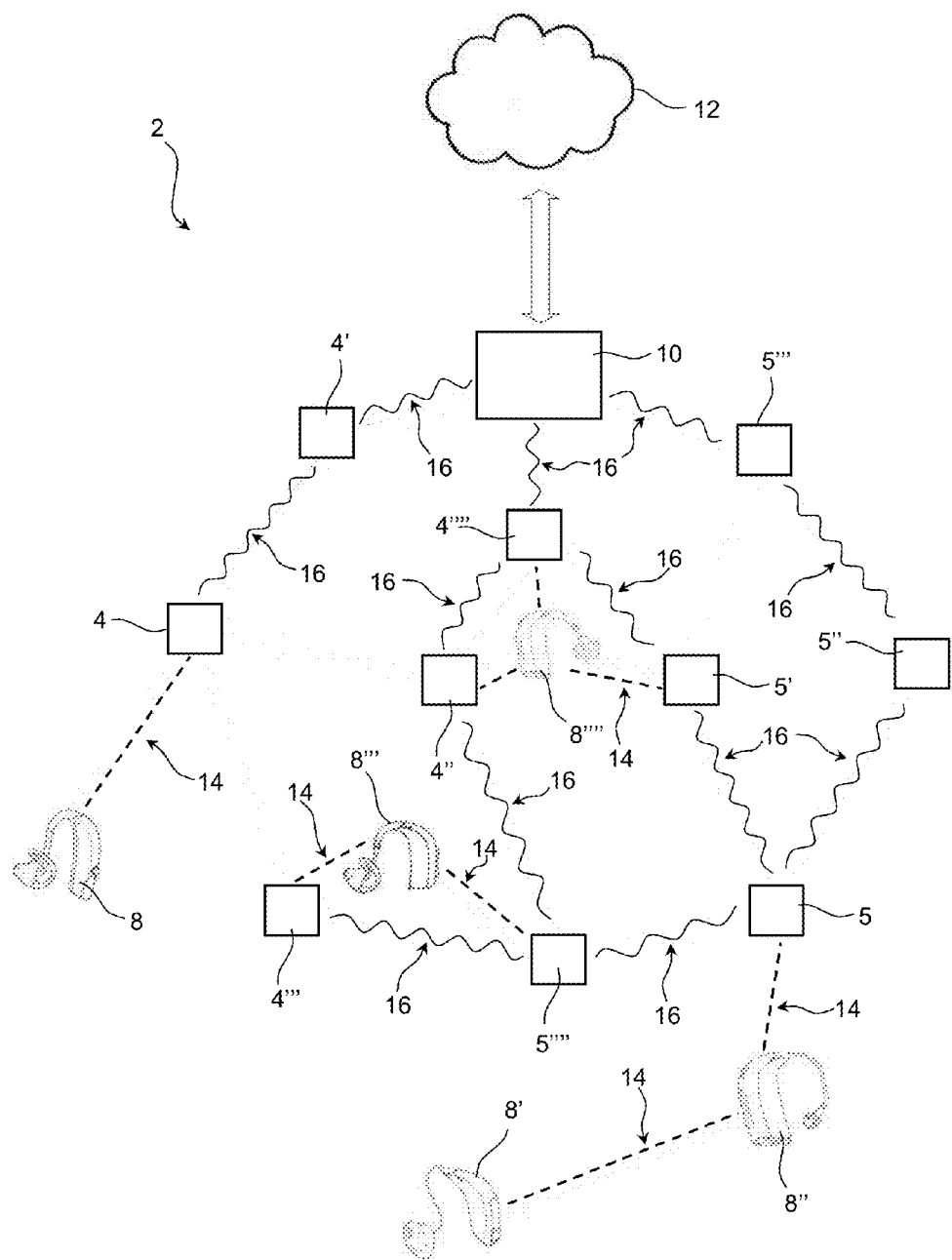
FIG. 2 shows another schematic view of a system according to an embodiment of the disclosure.

FIG. 2 illustrates a schematic view of a system 2 according to an embodiment of the disclosure. The system comprises a first hearing device, collectively referred to as a hearing aid 8, configured to wirelessly communicate with a first access point 4 by means of a first wireless data connection 14. The first wireless data connection 14 is configured to communicate wirelessly with a second access point 4' by means of a wireless data connection 16. The second access point 4' is configured to communicate wirelessly with a central unit 10 by means of a wireless data connection 16. The central unit 10 is configured to communicate via the Internet 12 in a cloud solution. Accordingly, the data received by the central unit 10 may be accessed through a remote unit (e.g. by a hearing care professional via the Internet 12).

The system comprises a second hearing device 8' configured to wirelessly communicate with a third hearing device 8" by means of a wireless data connection 14. The third hearing device 8" is configured to communicate wirelessly with an access point 5. The access point 5 is configured to communicate wirelessly with three different access points 5', 5", 5''' by means of wireless data connections 16.

The system comprises a fourth hearing device 8' configured to wirelessly communicate with access points 4''' and 5'''' by means of wireless data connections 14. The access points 5'''' communicates wirelessly with an access point 4" by means of a wireless data connection 16.

The system comprises a fifth hearing device 8'''' configured to wirelessly communicate with access points 4", 4'''' and 5' by means of wireless data connections 14. The access points 4" communicates wirelessly with the access point 5'''' and the access point 4'''' by means of wireless data connections 16. The access points 5' communicates wirelessly with the access point 5 and the access point 4'''' by means of wireless data connections 16.

The access points 5" communicates wirelessly with an access point 5''' by means of a wireless data connection 16 and the access points 5''' communicates wirelessly with the central unit 10 by means of a wireless data connection 16.

The wireless data connection 14 (indicated with dotted lines) between the hearing devices 8, 8', 8", 8''', 8'''' and the access points 4, 4', 4", 4''', 4'''', 5, 5', 5", 5''' may be conducted by using any suitable communications protocol, including Bluetooth Low Energy (Bluetooth Smart) and wireless LAN.

The wireless data connection 16 (indicated with arced lines) between different access points 4, 4', 4", 4''', 4'''', 5, 5', 5", 5''' and between the access points 4, 4', 4", 4''', 4'''', 5, 5', 5", 5''' and the central unit 10 may be conducted by using any suitable communications protocol, including a wireless local area network (WLAN), WIFI, Bluetooth or other wireless networking technology.

A hearing care professional is preferably provided with access to the data received by the central unit 10 through a remote unit (e.g. by via the Internet/Cloud 12).

Figure 3:
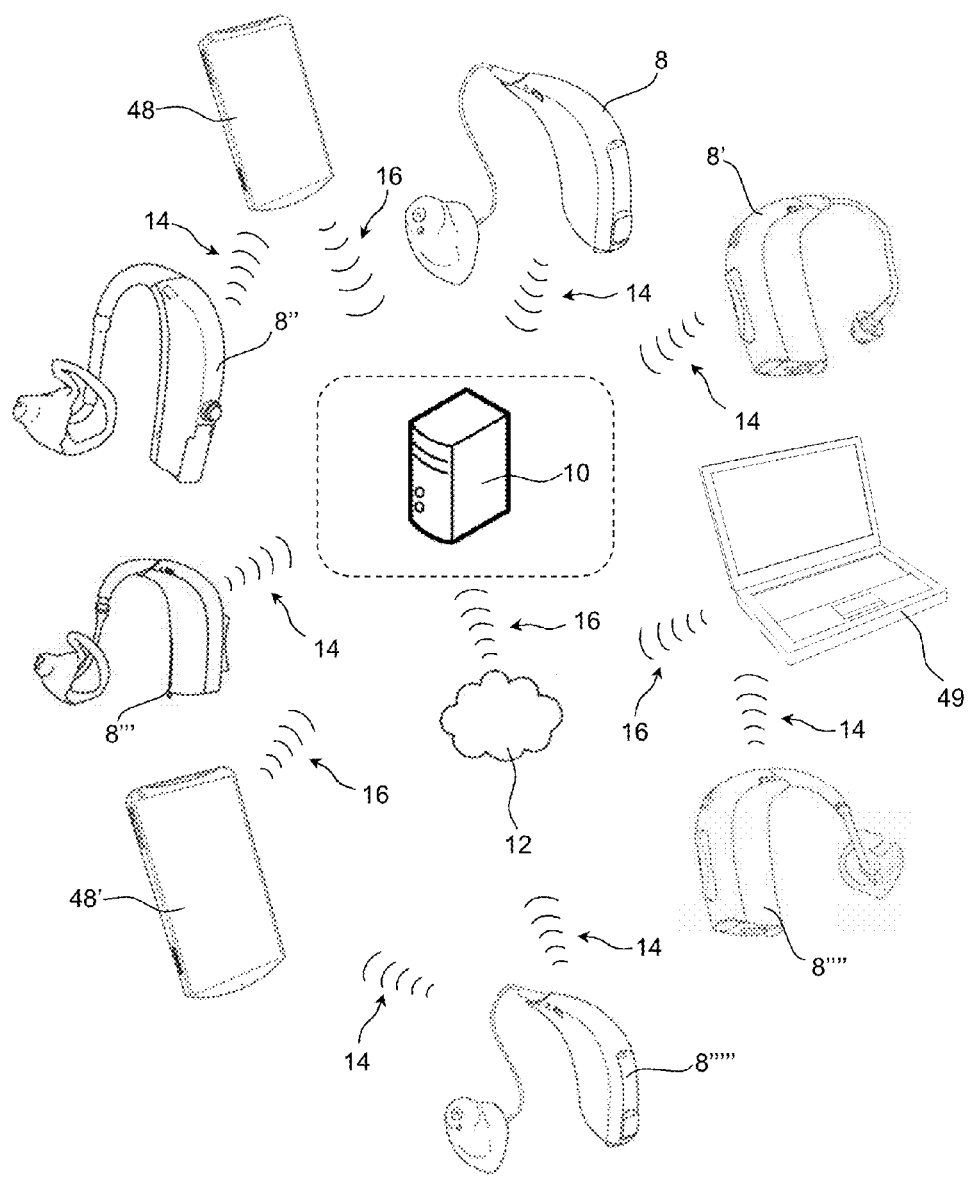
FIG. 3 shows a schematic view of how data is communicated from hearing devices towards a central unit in a system according to an embodiment of the disclosure.

FIG. 3 illustrates a schematic view of how data is communicated from hearing devices 8, 8', 8", 8''', 8'''', 8''''' to a central unit 10 in a system according to an embodiment of the disclosure. The system comprises a first hearing aid 8 configured to wirelessly communicate directly with a central unit 10 by means of a wireless data connection 14. The system moreover comprises a second hearing aid 8' configured to wirelessly communicate directly with the central unit 10 by means of a wireless data connection 14.

The system moreover comprises a third hearing device 8" configured to wirelessly communicate with a smartphone 48 by means of a wireless data connection 14. The smartphone 48 is configured to communicate wirelessly with the central unit 10 by means of a wireless data connection 16.

The system moreover comprises a fourth hearing device 8''' configured to wirelessly communicate directly with the central unit 10 by means of a wireless data connection 14.

The system moreover comprises a fifth hearing device 8'''' configured to wirelessly communicate directly with a computer 49 by means of a wireless data connection 14. The computer 49 communicates via the Internet/cloud 12 by means of a data connection 16. There is a data connection 16 between the Internet/cloud and the central unit 10.

The sixth hearing device 8''''' communicates wirelessly with a smartphone 48' configured to communicate with the central unit 10 by means of a wireless data connection 16. The sixth hearing device 8''''' communicates wirelessly via the Internet 12 by means of a wireless data connection 14.

The hearing devices 8, 8', 8", 8''', 8'''', 8''''' may either communicate directly with the central unit 10 or by means of an intermediate device 48, 48', 49. The data received by the central unit 10 may be accessed through a remote unit (e.g. by a hearing care professional via the Internet 12). Accordingly, the system according to the disclosure provides access to data transmitted by the hearing devices 8, 8', 8", 8''', 8'''', 8''''' in an easy manner even from a remote location. Therefore, the data transmitted by the hearing devices 8, 8', 8", 8''', 8'''', 8''''' may be applied to increase the comfort of the hearing device user and to provide a way of determining the correct time of service or replacement of elements such as the battery.

Figure 4:
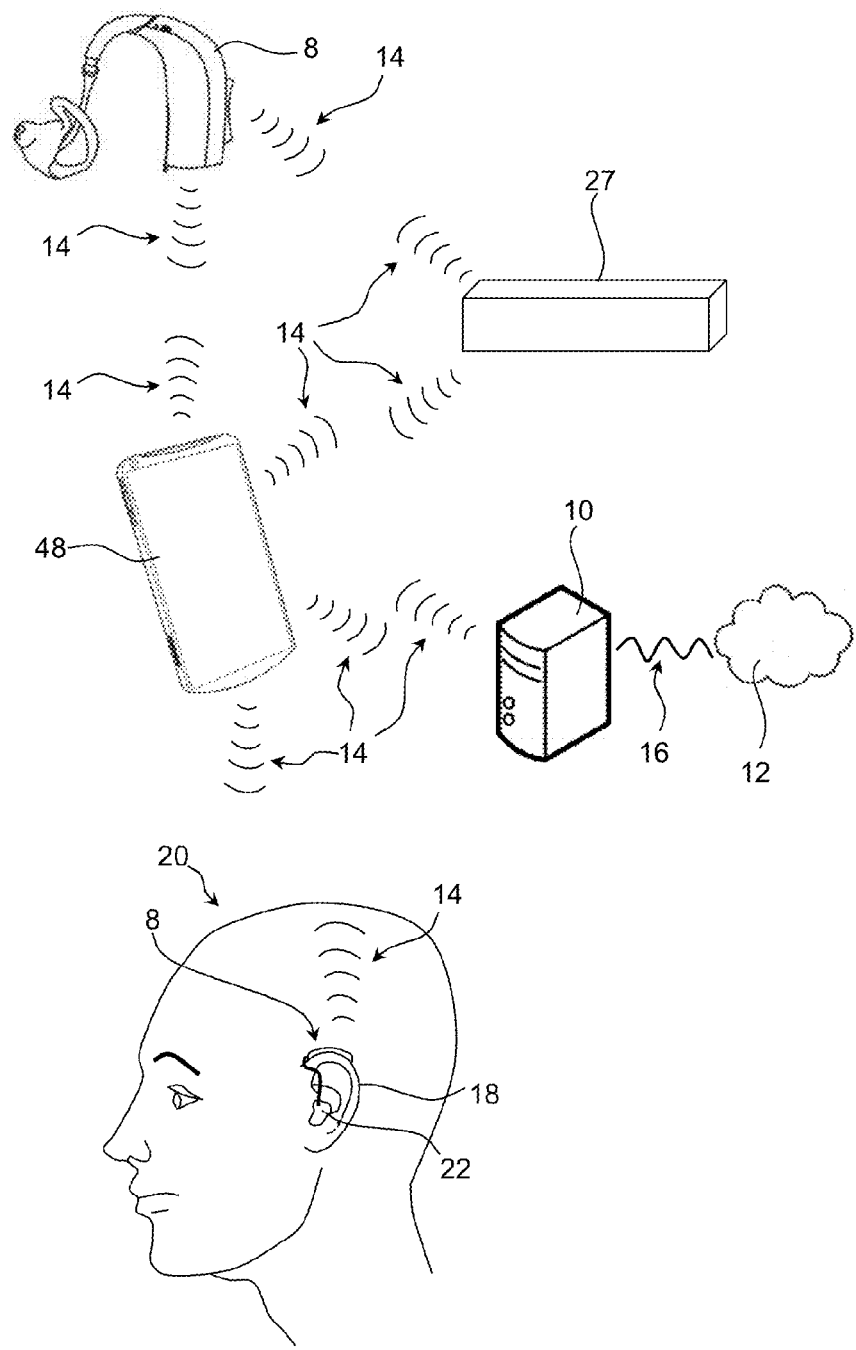
FIG. 4 shows a schematic view of a hearing aid user wearing a hearing device provided with a sensor.

FIG. 4 shows a schematic view of a hearing aid user 20 wearing a hearing aid 8 provided with a sensor, wherein the hearing device 8 is configured to communicate wirelessly directly or indirectly with a central unit 10.

In the bottom part of FIG. 4, a schematic view of a hearing aid user 20 is shown. The hearing aid user 20 is wearing a behind-the-ear (BTE) hearing device 8 behind the ear 18, wherein the speaker 22 has been positioned in the ear canal. The hearing device 8 is equipped with a sensor and a communication unit configured to communicate wirelessly with communication devices 48 in the surroundings of the hearing aid user 20.

In the top part of FIG. 4, a schematic view of a hearing device 8 is shown. The hearing device 8 communicates wirelessly with a smartphone 48 that is communicating wirelessly with a central unit 10 formed as a server 10. An auxiliary device 27 is provided next to the hearing device 8 in FIG. 4. The auxiliary device 27 may communicate wirelessly with the smartphone 48 and the hearing device 8.

The hearing aid 8 may be configured as a health monitoring hearing aid 8 configured to measure the electrical activity of the brain by using electroencephalography (EEG). The hearing device 8 may therefore comprise sensors for detecting EEG signals and a unit for transmitting the detected EEG signals, descriptions of the EEG signals, or decisions based on the EEG signals to the smartphone 48 or another suitable device. The hearing device 8 may comprise sensors configured to detect or estimate one or more of the following parameters: heart rate, heart rate variability, oxygen saturation (level of oxygen), blood pressure and level of sugar in the blood, body temperature, bioelectrical impedance, skin conductance, ultraviolet (UV) exposure, acceleration, vibration, pH, bacteria concentration, blood glucose level. The hearing device 8 may comprise an accelerometer, a pH sensor, a pH sensitive-coating, a blood glucose meter or printed pigments as a chemical sensor for bacteria by way of example. The sensors may be integrated in the ear piece of the hearing device (e.g. a dome or an ear mould).

The smartphone 48 may be replaced by another device capable of providing the required communication. Such devices may include a tablet, PC, and wearable devices as Smartwatches and Smartglasses. The device may contain one or more microphones.

Sensor data received by the central unit 10 can be communicated wirelessly via the Internet 12 by means of a wireless data connection 16. Hereby, the data can be accessed by a hearing care professional from a remote location.

The wireless data connections 14 may be conducted by using any suitable communications protocol, including Bluetooth Low Energy (Bluetooth Smart) and wireless LAN. The wireless data connection 16 (indicated with an arced line) between the central unit 10 and the Internet 12 may be conducted by using any suitable communications protocol, including a wireless local area network (WLAN), WIFI, Bluetooth or other wireless networking technology.

FIG. 5A) illustrates a schematic perspective view of a hearing aid 8 according to an embodiment of the disclosure. The hearing aid 8 comprises an ear piece 30 provided with sensors 24, 26, 28 and a speaker 22. The sensors 24, 26, 28 protrude from the surface of the ear piece 30. The ear piece 30 is connected to the housing 34 of the hearing aid 8 by a tube 32. The hearing aid 8 is a BTE style hearing device 8 with sensors with electrodes 24, 26, 28 formed for example as electrodes.

The hearing aid 8 is a health monitoring hearing aid 8 configured to measure EEG signals, process the EEG signals, or transmit the EEG data to an external receiver like a smartphone for further processing there or in the cloud. The hearing aid 8 may be configured to apply the EEG signals to estimate heart rate and/or heart rate variability.

In one embodiment according to the disclosure, the hearing aid 8 is configured to be a built-in or associated with part of a sports monitoring and training program. The sensor data from the hearing aid 8 may be applied to quantify/estimate the overall mental energy of the wearer at the time of the exercise.

Over time, the hearing aid 8 will provide sensor data including the mental energy after exercise. Accordingly, the hearing aid 8 may be capable of predicting the benefit of a given exercise and optimise the mental energy for the rest of the day by modifying the exercise program.

The hearing aid 8 may be configured to interact with the wearer by playing sounds to signal changes, e.g. saying: go slower, go faster, and increase intensity. Furthermore, the hearing aid may be configured to generate guiding input in form of beeps or other non-speech sounds or via visual indicators on a smartphone.

The hearing aid may be configured to be set into one or more "sports modes" associated to one or more different sound processing schemes. In one embodiment of the disclosure, the hearing aid 8 is configured to detect the heart rate level, preferably based on a detected EEG signal, and apply the detected or estimated heart rate to set the hearing aid 8 in a sport mode. It may be beneficial that the hearing aid 8 is configured to compensate for the distortions of spatial perception imposed by either blocking the ear canal with an ear mould or a hearing aid, and the altered spatial cues due to microphone positions.

In one aspect of the disclosure, the hearing aid is configured to prioritise sound sources approaching the wearer from behind. Moreover, the hearing aid 8 may be configured to prioritise speech sounds with alerting prosody, e.g. an animated watch out.

FIG. 5B) shows a schematic perspective view of another hearing aid 8 according to an embodiment of the disclosure. The hearing aid 8 comprises a built-in sensor integrated in the ear mould of the hearing aid 8. It is possible to apply a built-in sensor in various types of hearing devices including receiver-in-the-ear (RITE), BTE, in-the-ear (ITE), completely-in-canal (CIC) and invisible in the canal (IIC) type hearing devices. The sensor may be a heart-rate sensor configured to continuously monitor the heart rate, analyze, and classify abnormal activity. The hearing device 8 may be configured to inform the hearing device user when it is recommended to consult a doctor.

Abnormal heart rhythm, either fast-fluctuating or continuously elevated, may be a sign of serious heart or circulatory diseases, which in some cases may indicate or lead to ventricular fibrillation (cause of 50% of all cardiac deaths), sudden cardiac death, fainting, or strokes. Prolonged increased heart rate, which may be indicative of cardiovascular risks, such as coronary artery disease (blockage in the pipes of the heart) may be detected by monitoring the heart rate.

The sensor may be optical, mechanical, or acoustical. When applying an optical sensor, the heart rate sensor can be formed as a small light emitter that transmits light towards a blood vessel in the ear canal and a sensor unit configured to measure the reflected light. This approach can also be used to measure/estimate oxygen levels in the blood.

When applying a mechanical sensor, the heart rate sensor can be formed as a sensor unit comprising an accelerometer placed on or close to the surface of the ear mould of the hearing aid 8. The sensor unit may be configured to detect vibration of the blood vessels under the skin of the ear mould. The hearing device may be configured to filter out noise (e.g. from other body movements) by using heart rate measurements conducted by means of the hearing device 8.

When applying an acoustical sensor, a small microphone 38 configured to pick up sound from the arteries surrounding the ear canal may be placed on the side of the ear mould as illustrated in FIG. 5C). Alternatively, vibrations from the blood vessels will excite the air in the ear canal (which makes it is possible to hear the heartbeat when blocking the ears with the fingers). This may be detected by a dedicated microphone 38 provided at the inner side of the ear mould.

The hearing device may preferably be configured to carry out signal processing in order to extract the heartbeat signal from the sensor. It is possible to apply a modulation analysis for this purpose.

The hearing aid 8 shown in FIG. 5B is configured to reduce the occlusion effect. The hearing aid 8 may be provided with a microphone configured to pick up body-transmitted sounds. The hearing aid 8 is provided with a first bore 42 for transmitting sound from the receiver (see FIG. 5C) of the hearing aid 8 towards the ear drum of the hearing aid user. The hearing aid 8 is provided with a second bore 44 for providing ventilation via the vent 40 shown in FIG. 5C.

FIG. 5C illustrates a schematic perspective view of a further hearing aid 8 according to an embodiment of the disclosure. The hearing device 8 is configured to be inserted into the ear canal. The hearing aid 8 comprises a vent 40 for preventing the occlusion effect. The hearing aid 8 is provided with a centrally arranged receiver 22 configured to generate and acoustically transmit sound through an opening in the front end of the hearing aid 8. The hearing device 8 is provided with a microphone connected to a first cross socket 36, whereas the receiver 22 is connected to another cross socket 36.

The hearing devices 8 shown in FIG. 5A, FIG. 5B and FIG. 5C are suitable for being used to track performance during fitness exercise and/or other health monitoring purposes. One main benefit is that the sensor resides in a hearing device already used by a hearing device user.

Detected data is preferably communicated to the Internet/cloud. The data (e.g. EEG-signals) may be used to estimate physical conditions and "mental energy": Accordingly, the data may be used to generate recommendations such as modifications of user behavior. The hearing device 8 may be configured to communicate with a smartphone.

According to an embodiment of the disclosure, the hearing device is configured to provide one or more acoustic reminders and/or warnings to the hearing aid user 20. A reminder may be generated on the basis on time (triggered by a setting in a personal calendar in a smartphone), location, body measures such as heart rate, temperature, EEG signals and indoor climate parameters such as temperature and humidity. The hearing aid may be used to provide scheduled reminders and also reminders and warnings caused by other events in the daily life. As cognitive skills decline with age, elderly hearing aid users 20 may have an added benefit from such features.

It may be an advantage that the hearing aid 8 is configured to generate a reminder and/or a warning can be triggered by the hearing aid 8 itself and by a smartphone 48 connected to the hearing device 8. The hearing aid 8 may be configured to generate a reminder and/or a warning on the basis of a calendar event in the calendar of the smartphone 48. The hearing aid 8 may be configured to generate a reminder and/or a warning related to medicine intake, wherein the reminder and/or a warning is generated by using a smartphone application that has the prescriptions stored and a Near Field Communication, (NFC) reader or a QR code reader or a bar code reader configured to detect and monitor a pillbox from which the medicine is taken.

The hearing aid 8 may be configured to generate an exercise reminder, triggered by calendar (time) or physical monitoring of the hearing aid user 20 directly from the hearing aid 8.

The hearing aid 8 may be configured to generate a reminder and/or a warning triggered by EEG signals detected by the hearing device 8.

The hearing aid 8 may be configured to detect that the hearing aid user 20 is falling asleep (by means of EEG signals detected by the hearing device 8) while driving a car.

The hearing aid 8 may be configured to detect parameters related to the local climate, e.g. moisture from rain or shower. If possible, this should be triggered before actual water drops hit the hearing aid. The hearing aid 8 may be configured to generate a reminder and/or a warning based on such detected climate related parameters.

The hearing aid 8 may be configured to detect parameters related to the location, e.g. a warning triggered by the location detected by a Global Positioning System (GPS) receiver. The hearing aid 8 may be configured to the distance to water (shoreline). Such warning may be generated in order to remind the user 20 to take the hearing aid 8 off, before going swimming.

Accordingly, the hearing aid 8 may be the centre of relevant acoustic notifications to the user 20. All reminders and/or warnings and/or alarms may preferably be spoken in clear language. The reminders and/or warnings and/or alarms may be postponed up to a defined time limit, if the surroundings are too noisy for a good playback. Likewise, it may be an advantage that a "repeat" feature is provided, in such a manner that if the user misses a reminder and/or warning and/or alarm, said reminder and/or warning and/or alarm should be visible on the smartphone 48.

Figure 6:
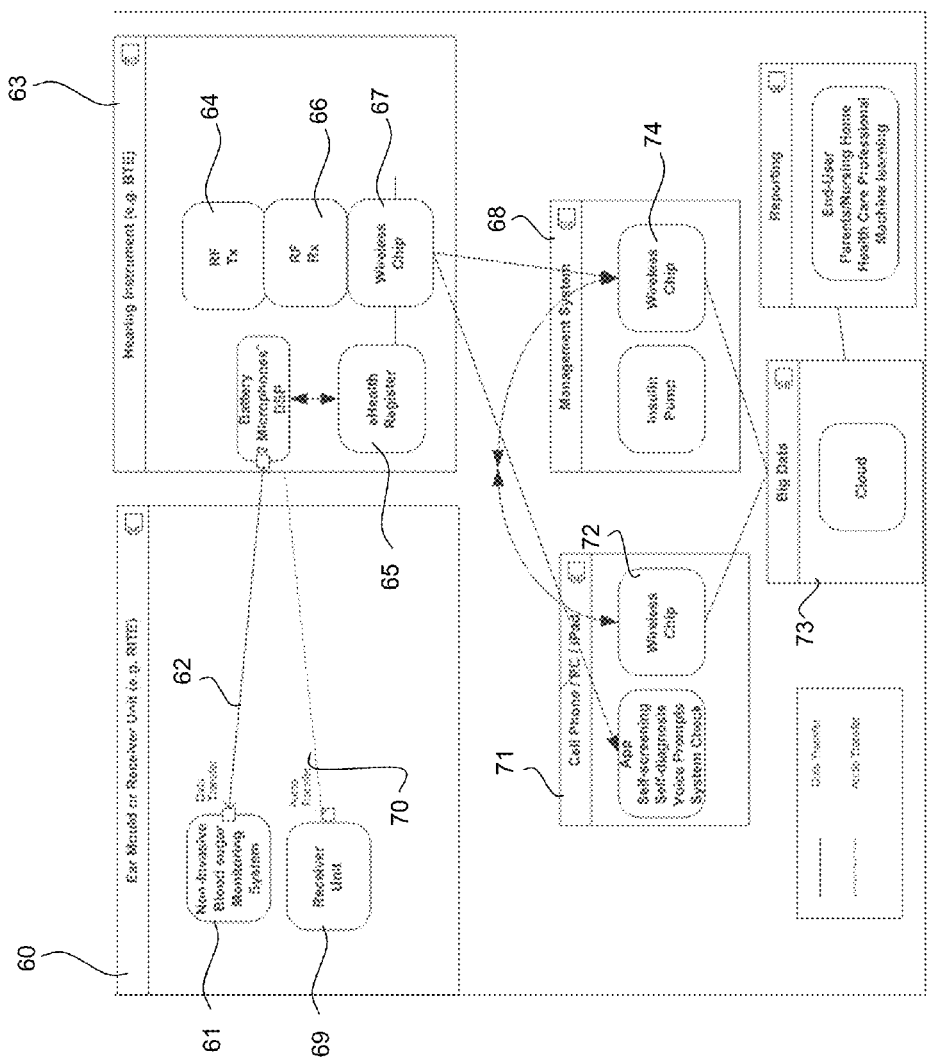
FIG. 6 shows a system for intelligent and wireless monitoring and management of diabetes in hearing devices.

FIG. 6 illustrates a system for intelligent and wireless monitoring and management of diabetes in hearing devices.

Diabetes results in abnormally high concentrations of glucose in the blood. Therefore, diabetic patients monitor their blood glucose levels in order to control when an antihyperglycemic agent such as insulin is required. Blood glucose monitoring is usually conducted by using an invasive method.

Diabetic patients manage high blood glucose levels with oral or injected antihyperglycemic agents such as insulin. Insulin can be injected manually or by means of an injection pump.

According to one aspect according to the disclosure, the system comprises a hearing aid provided with a wireless chip configured to support non-invasive blood glucose level monitoring. It may be an advantage that the wireless chip is configured to enable ongoing and intelligent diabetes monitoring and management e.g. by communicating with Internet of Things (IoT) devices.

According to an embodiment of the disclosure, the system comprises a hearing aid provided with a blood glucose meter that does not require pricking. Such blood glucose meter may be a biochip configured to measure glucose through non-invasive dermatological patches or in body fluids such as saliva, electrochemical sensors, or mid-infrared light sensors. It is possible to apply a sensor that monitors glucose sugar levels without needing pricking. Such sensor may be implemented in a hearing aid according to the disclosure. It is possible to provide an implementation of a non-invasive dermatological patch on the surface of the ear mould or receiver unit.

FIG. 6 shows a system for intelligent and wireless monitoring and management of diabetes in hearing devices, such as hearing aids. As indicated, an ear mould or a receiver unit 60 of a hearing aid (such as a RITE by way of example) is provided with a sensor 61 configured to conduct a non-invasive blood sugar monitoring. This sensor 61 is configured to communicate 62 with the other parts of the hearing aid, such as a BTE unit 63, which is configured to communicate with an integrated register 65. The hearing aid comprises a radio frequency transmitter unit (RF Tx) 64 and a radio frequency receiving unit (RF Rx) 66 connected to a communication unit 67 configured to communicate wirelessly with an external management system 68 and an external electric device (e.g. a smartphone, a computer or a tablet). The receiver unit 69 of the hearing aid is configured to receive audio data 70 sent from the hearing aid. The hearing aid comprises a digital signal processing device (DSP), one or more microphone and a battery.

The external electric device 71, such as a cell phone, ipad or computer comprises a communication unit 72 configured to receive information from the hearing device and to transmit information to an external system indicated as "big data" 73. The external system is configured to transfer data to end-users including but not limited to parents, nursing homes, health care professionals and other suitable receivers.

The external management system 68 comprises a communication unit 74 configured to communicate (e.g. wirelessly) with the external electric device and/or with the external system indicated as "big data" 73. The external management system 68 may be a device comprising an insulin pump and a communication unit.

The solid lines indicate data transfer while the dotted line indicates audio transfer.

By using a system as shown in FIG. 6, it is possible to improve the medical treatment of diabetic hearing device users.

Figure 7:
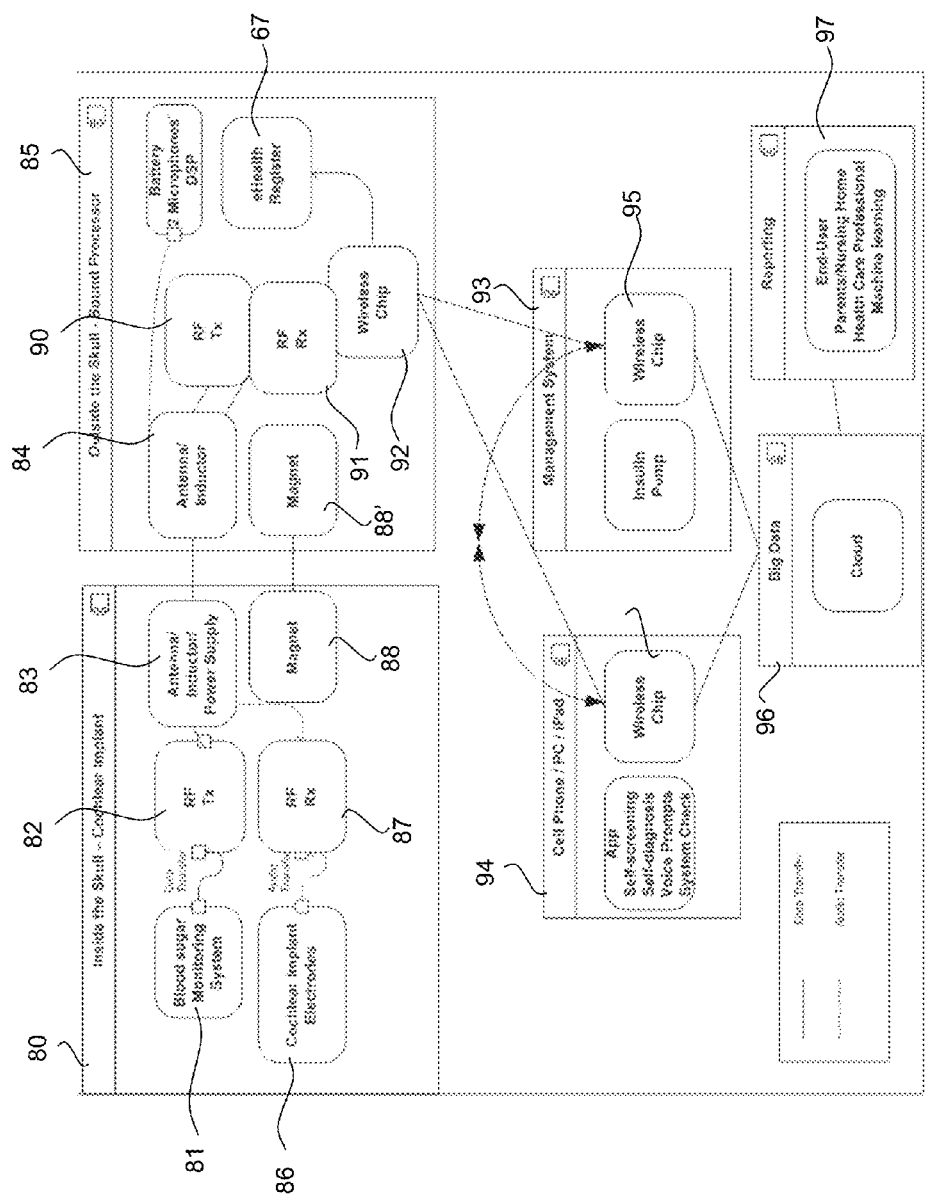
FIG. 7 shows a system for intelligent and wireless monitoring and management of diabetes in a cochlear implant.

FIG. 7 shows a system for intelligent and wireless monitoring and management of diabetes in a cochlear implant, wherein the implantation of a blood glucose meter is part of the cochlear implant. Inside the skull 80, the cochlear implant is provided with a blood sugar monitoring system 81 configured to transfer data to a radio frequency transmitter device 82 connected to an antenna/inductor 83 for communicating with a corresponding antenna/inductor 84 provided within the sound processor unit outside the skull.

The cochlear implant is provided with cochlear implant electrodes 86 configured to communicate (data transfer) with a radio frequency receiver device 87 connected to the antenna/inductor. The sound processor unit is attached to the skull by magnetic attraction 88 between corresponding magnets 88' provided as part of the implanted cochlear implant and as part of the sound processor unit. The sound processor unit comprises a digital signal processing device (DSP), one or more microphone and a battery.

The sound processor unit 85 is configured to communicate with an integrated register 89. The sound processor unit comprises a radio frequency transmitter unit 90 (RF Tx) and a radio frequency receiving unit (RF Rx) 91 connected to a communication unit 92 configured to communicate wirelessly with an external management 93 system and an external electric device 94 (e.g. a smartphone, a computer or a tablet).

The external electric device 93, such as the external management system, comprises a communication unit 95 configured to receive information from the hearing device and to transmit information to an external system indicated as "big data" 96. The external system indicated as "big data" 96 is configured to transfer data to end-users 97 including but not limited to parents, nursing homes, health care professionals and other suitable receivers.

The cochlear implant may include i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an embodiment, the hearing aid comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in the cochlea when the carrier is inserted in cochlea.

Figure 8:
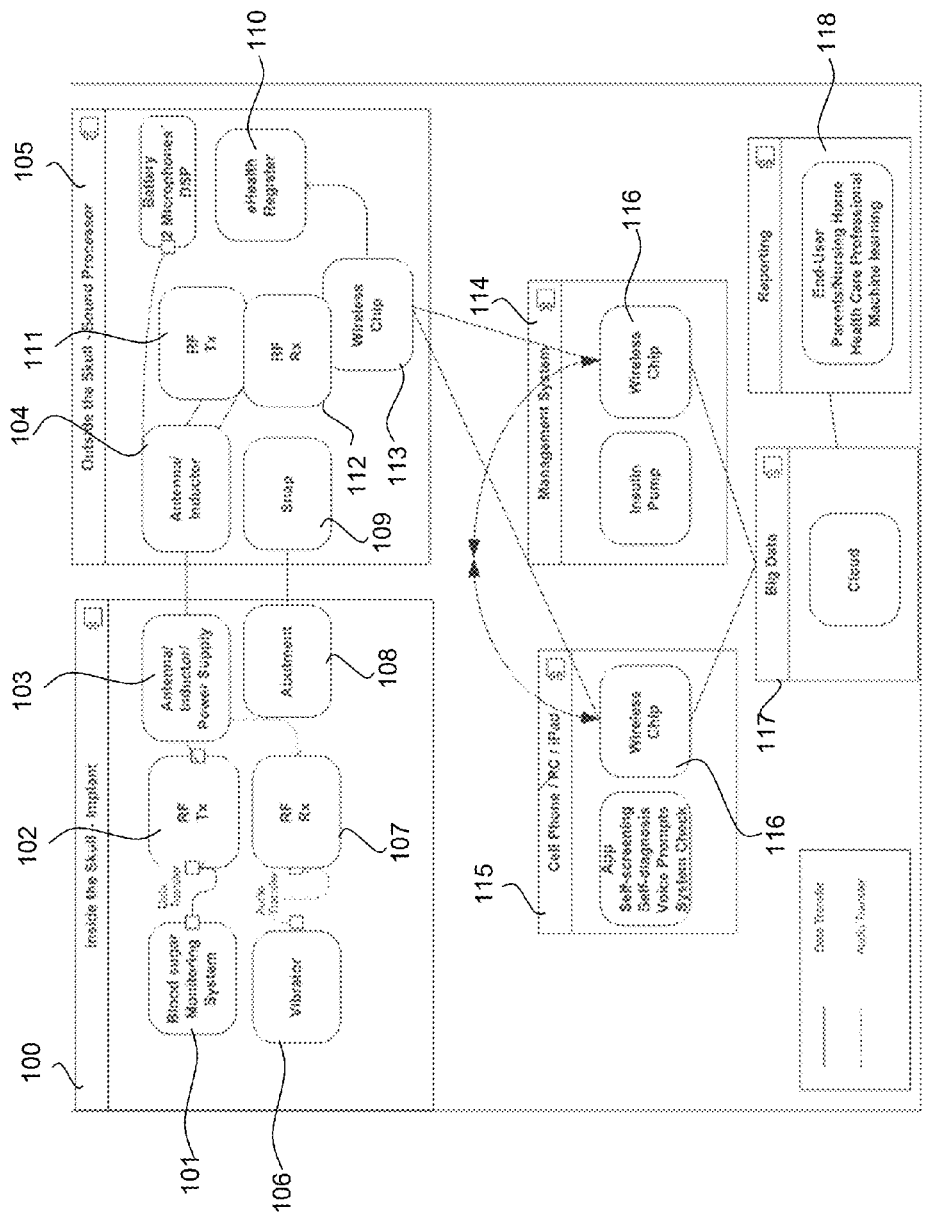
FIG. 8 shows a system for intelligent wireless monitoring and management in a bone-anchored hearing system.

FIG. 8 shows a system for intelligent and wireless monitoring and management of diabetes in a bone-anchored hearing system (BAHS), wherein the implantation of a blood glucose meter is provided as part of the BAHS.

Inside the skull, the cochlear implant 100 is provided with a blood sugar monitoring system 101 configured to transfer data to a radio frequency transmitter device 102 connected to an antenna/inductor 103 for communicating with a corresponding antenna/inductor 104 provided in the sound processor unit 105 outside the skull.

The implant is provided with an implant vibrator 106 configured to receive data from a radio frequency receiver device 107 connected to the antenna/inductor 103. The sound processor unit 105 is attached to the skull by means of a snap 109 (being part of the sound processor outside the skull) and an abutment 108 provided as part of the implant. The sound processor unit comprises a digital signal processing device (DSP), one or more microphone and a battery.

The sound processor unit 105 is configured to communicate with an integrated register 110. The sound processor unit 105 comprises a radio frequency transmitter unit (RF Tx) 111 and a radio frequency receiving unit (RF Rx) 112 connected to a communication unit 113 configured to communicate wirelessly with an external management system 114 and an external electric device 115 (e.g. a smartphone, a computer or a tablet).

The external electric device 115 comprises a communication unit 116 configured to receive information from the hearing device and to transmit information to an external system indicated as "big data" 117. The external system indicated as "big data" 117 is configured to transfer data to end-users 118 including but not limited to parents, nursing homes, health care professionals and other suitable receivers.

In the system explained with reference to FIG. 6, FIG. 7 and FIG. 8, it is possible to apply applications for any communication platform including iPad/Android/Windows.

The diabetes management software can communicate in the form of radio frequency communication to both the monitoring and the management devices. The system comprises a storage unit for storing blood glucose levels and insulin regimens for later retrieval and/or display of trends over time, with the option to send the information to end-users and third parties such as parents/nursing homes and health care professionals.

The systems disclosed in FIG. 6, FIG. 7 and in FIG. 8 are configured to detect levels outside the normal range (wherein the normal range level may be individualised, e.g. set by a health care professional). The system may be provided with diabetes management software configured to prompt suitable management in the form of insulin OR in the form of lifestyle advice parameters, e.g. a diet or exercise regimen. The systems may be configured to communicate suitable management to the end-user with voice prompt via the hearing device.

The systems described with reference to FIG. 6, FIG. 7 and FIG. 8 are configured to allow the user to conduct self-screening and self-diagnosis of diabetes. Diabetes diagnosis is typically done with a glucose tolerance test which can be self-administered.

The data generated by the management and monitoring systems can be used to optimise clinical decisions through machine learning and artificial intelligence (à la IBM's Watson). This optimisation can be carried out at a patient level or at a population level.

FIG. 9A) to 9C) illustrates a health monitoring system using hearing devices with a wireless link. Elderly hearing aid users are typically old people who may experience health issue from day to day or subtle changes over a longer time period. Examples may range from reduced daily water intake causing dehydration to slow-growing tumors in the head. Bilateral hearing aids are in the perfect location for monitoring changes to the head. Accordingly, in these embodiments, a first sensor is arranged in connection with a first hearing device, and a second sensor is arranged in connection with a second hearing device of a user, wherein said first sensor is configured to transmit a signal to set said second sensor and said second sensor is configured to receive a signal from said first sensor. That is, a first hearing aid is arranged on one ear of a user and the second hearing aid is arranged on the second ear of a user, wherein the two hearing aids are able to transmit and receive data from each other.

The hypothesis is that the magnetic/electric conductance in the head varies with the relative water level in the head (short term) or pathologic anatomical changes (long term). This can be measured as the signal strength and signal spectrum on the receiving side at regular intervals. Either inductive near link or electric 2.4 GHz can be used depending on which system is most sensitive to the health parameters of interest. Special radio frequency signals on the state of the art hardware may also be applied for this purpose alone.

FIG. 9A illustrates a schematic view of a hearing device user 20 drinking a soft drink or water 50 in response to a thirst signal generated in a brain tissue 54 of the brain 52.

According to an embodiment of the disclosure, the system comprises one or two hearing devices 8, 8' configured to measure the "water level" in the brain 52 of the hearing device user 20. The "water level" in the brain 52 of the hearing device user 20 may be measured in several ways. If the water level is below a predefined threshold for the hearing device user 20, a "reminder signal" is generated by at least one of the hearing devices 8, 8' and sent to the user via e.g. a smartphone 48 or as a direct audio reminder, e.g. a speech message. Accordingly, the user is reminded to drink something as shown in FIG. 9A.

According to an embodiment of the disclosure, the system comprises one or two hearing devices 8, 8' configured to measure the relative water level and log the measurements at regular intervals in order to store in at least one of the hearing devices 8, 8'. Hereafter, the information can be uploaded to the cloud/Internet 12 for use by e.g. a physician to monitor the wellbeing of the hearing device user 20 as shown in FIG. 9B that illustrates a schematic view of a left and right hearing device 8, 8' communicating with a smartphone 48 and via the Internet 12.

FIG. 9C illustrates a hearing device user 20 wearing a first hearing device and second hearing device. The first hearing device transmits a signal 56 that is received by the second hearing device as a received signal 58. That is, a first sensor is arranged in connection with a first hearing device, and a second sensor is arranged in connection with a second hearing device of a user, wherein said first sensor is configured to transmit a signal to said second sensor and said second sensor is configured to receive a signal from said first sensor. In this way changes in the signals across the brain can be detected and used for diagnostic purposes.

In FIG. 9C, the right hearing device is acting as transmitter and the left hearing device is acting as receiver. The chemical composition of the brain 52 and the anatomy both affect the signal at the receiving end. Via reference data stored in the hearing devices and logging of key parameters over time, the short-term and long-term deviations can be measured and used to inform the hearing device user 20 and/or a physician, depending on the nature of the problem.

It is possible to measure the radio conductance and estimate the physical state of the brain 52 on the basis of these measurements.

In the event of serious changes, such as a tumour in the brain 52 of a hearing device user 20, even small trends deviating from normal can be detected via logging and sent to the physician who then decides when to call the hearing device user 20 for further investigation. The method is completely non-invasive and does not require additional hardware components, e.g. electrodes in the ear canal. It may be preferred that the hearing device user 20 is never informed directly of this because it may lead to unnecessary concerns.

According to another embodiment of the disclosure, the system comprises one or two hearing devices 8, 8' provided with a dehydration measuring circuitry. Accordingly, it is possible to provide improved hearing devices 8, 8'. The hearing devices 8, 8' already contain a power source, loudspeaker (e.g. to produce alerts) and processing device(s) (DSP, MCU). The dehydration measuring circuitry may be configured to perform the dehydration measurement as a "bodily fluid" measurement conducted by detecting an impedance measurement of the internal and external tissue fluid (giving an "2R-1C" equivalent network) over a frequency range (e.g. 5-100 kHz). A four-electrode measurement may be used for increasing the accuracy; the AC current level may be 40 uA. The degree of dehydration may be detected as a change within the impedance pattern. Such solution is easy to implement since the hearing device is already in direct contact with the skin.

It is possible to apply a hearing device configured to contact a recording device in the form as a smartphone, a computer or another device by which it is possible to alert/inform caregivers. The connection between the hearing device and recording devices can be either wireless or wired.

According to a further embodiment of the disclosure, the system comprises a hearing device 8, 8' configured to provide an audible warning and/or send an alert to a smartphone that may be configured to warn a caregiver by Short Message Service (SMS) and/or send alerts to a more centralized system (PC or Smart Home/Smart Nursery Home Hub) and/or log the detected data when dehydration is detected.

The dehydration measurement function can be either a part of a hearing device or used by a non-hearing device user. For non-hearing device users, a caregiver can hand out a device and setup the measurement parameters and/or alarms.

Figure 10:
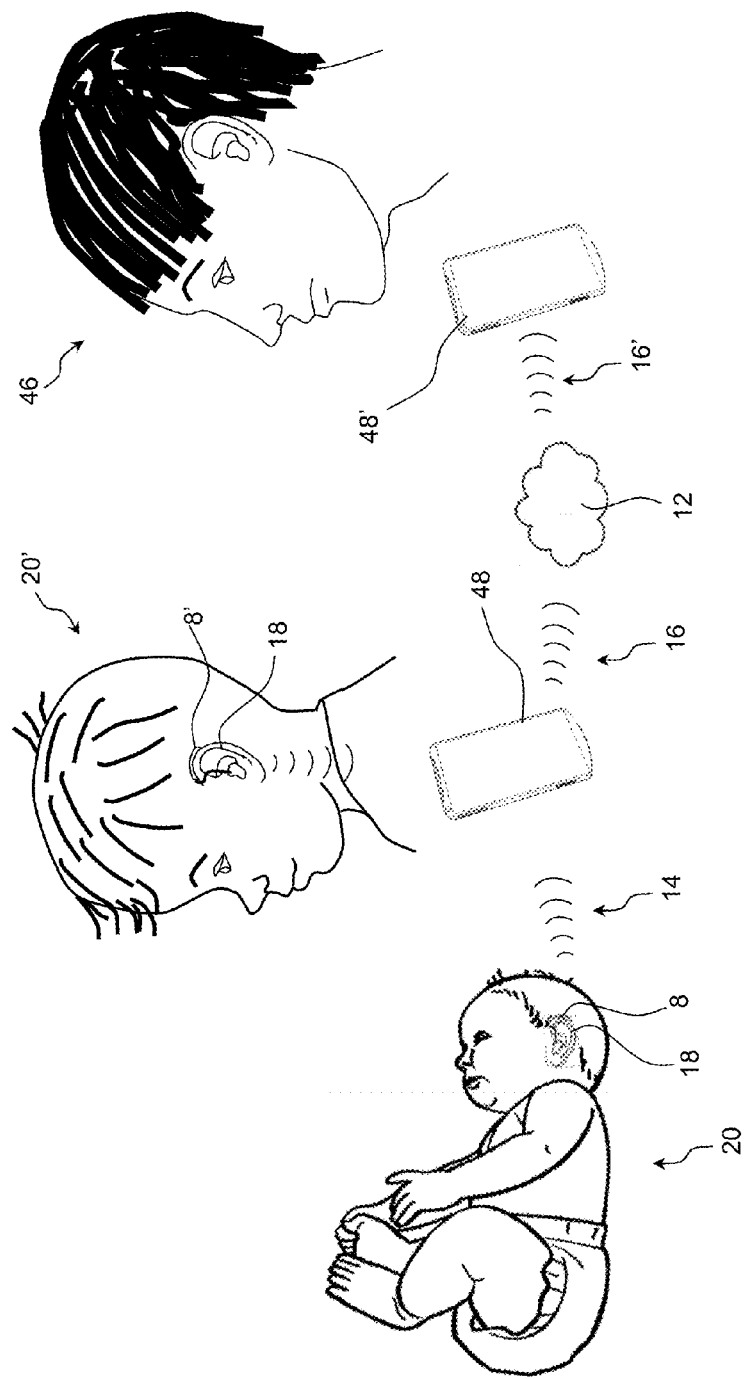

FIG. 10 illustrates a first hearing device user 20 (a baby) and a second hearing device user 20' (a child). The hearing device users 20, 20' are using wearable health monitoring hearing devices 8, 8' according to one aspect of the disclosure.

Many health conditions go undetected and untreated, with consequences ranging from minimal to death. For example, body temperature; pulse, blood pressure, and level of oxygen and sugar in blood; skin conductance; UV exposure; sudden acceleration, and dermatologic health could be better monitored, and therefore abnormal levels could be addressed.

Fever is a very prevalent clinical sign where body temperature increases above 38° C. Especially in children, fever is an important clinical sign with potentially severe consequences if undetected and untreated.

Pulse (tactile arterial palpation of the heartbeat), arterial blood pressure (pressure exerted by circulating blood upon the walls of blood vessels), level of oxygen in blood (arterial oxygen saturation of functional hemoglobin) or level of sugar in blood (glucose levels: hyperglycemia from diabetes mellitus or hypoglycaemia) are four vital signs that can inform about a person's health status.

Skin conductance (galvanic skin response) is the electrical conductance of the skin: it increases when the amount of sweat on the skin increases. Sweat is controlled by the sympathetic nervous system, so skin conductance is an indicator of psychological or physiological arousal and of stress.

Ultraviolet (UV) light through sun exposure affects human health: UVB radiation induces production of vitamin D in the skin. However, overexposure to UVB radiation causes some forms of skin cancer.

Sudden acceleration can be a sign of a fall, for example in the elderly or in people prone to seizures.

Dermatologic conditions at the level of the outer ear and ear canal such as otitis externa (external otitis or swimmer's ear), dermatitis (eczema), and psoriasis are common. Otitis externa has a prevalence of more than 1% over a 12-month period in the UK1. Otalgia (ear pain), otorrhea (ear discharge), and swelling are uncomfortable and can interfere with hearing aid use, for example by causing hearing aid feedback. The mechanisms of these conditions are varied (no infection, bacterial infection, or fungal infection).

Monitoring is possible and there is a general trend towards self-monitoring of health status and wearable technology. For example, a national telephone survey conducted by the Pew Research Center's Internet & American Life Project found that 69% of U.S. adults keep track of at least one health indicator such as weight, diet, exercise routine, or symptom. However, monitoring is often done only on-demand (not continuous) and from different sensors built in different devices. It would be relevant to collect self-monitoring sensors into one device worn continuously.

In one aspect of the disclosure, one or more parameters are detected by one or more sensors. Hereby, it is possible to monitor physiological states and detect abnormal states through hearing devices and other devices worn at the ear 18 of a hearing device user 20, 20'. Hearing devises may include hearing aids, cochlear implant speech processors and headphones (used with mobile devices).

As hearing devices are worn at the ear level for many hours daily (or worn continuously, for example with deeply inserted hearing aids), they allow for online monitoring. Monitoring of the parameters mentioned above could be obtained in several ways.

In one aspect of the disclosure, a thermometer is integrated to the hearing device. The thermometer may be similar to the infrared ear thermometers currently available on the market. Alternatively, a thermosensitive coating that changes colour according to temperature could be used along with a) a system where the wearer or another person can take a picture of the coating colour with a mobile device for automated diagnosis or b) a "legend" of which colours are indicative of fever, for manual comparison by the wearer or another person.

In another aspect of the disclosure, a pulse and blood pressure sensor (sphygmomanometer) and/or an oxygen in blood sensor (pulse oximeter or functional near-infrared spectroscopy) and/or a sugar in blood sensor (with or without using pricking) is integrated into hearing device 8, 8'.

According to a further aspect of the disclosure, the hearing device 8, 8' is provided with an integrated heart rate sensor comprising an additional hearing aid microphone in the ear canal or near the vent entrance and monitoring the compliance of the middle ear using conventional 226 Hz compliance measurement. Given the artery running close to the tympanic membrane, the microphone can record the beating frequency (pulse) as changes in the middle ear compliance.

According to an even further aspect of the disclosure, the hearing device 8, 8' is provided with an integrated heart rate sensor comprising ultra-sensitive mechanical sensors configured to detect pulse on body parts.

Monitoring heart rate in a hearing aid can also be used as an input to a health and fitness application on a mobile device 48, 48'.

According to an even further embodiment of the disclosure, the hearing device 8, 8' is provided with an integrated sugar level sensor configured to detect the sugar level in the blood by means of an electrochemical sensor, shaped as a biochip that measures sugar by means of a mid-infrared light sensor.

According to another embodiment of the disclosure, the hearing device 8, 8' is provided with a galvanic skin response sensor integrated into the hearing device 8, 8'.

According to a further embodiment of the disclosure, the hearing device 8, 8' comprises a UV exposure sensor integrated into the hearing device 8, 8'. Hereby, it would be possible for parents to determine when to provide vitamin D supplements to their children or when to reapply sunscreen during sun exposure.

According to a further aspect of the disclosure, the hearing device 8, 8' comprises an accelerometer integrated into the hearing device 8, 8'.

According to an even further aspect of the disclosure, the hearing device 8, 8' comprises a pH sensor/pH sensitive-coating/printed pigments as a chemical sensor for bacteria integrated into the hearing device 8, 8'.

Monitoring could have a range of applications, for example for screening or diagnosis of health conditions or for monitoring of health status. For example, a person who is under post-operative care could be discharged from the hospital earlier if wearing a monitoring device connected to the hospital that could monitor e.g. changes in blood pressure or pulse. Monitoring of the parameters mentioned in the section above could either be always active ("online" or "continuous") or only active on demand. On demand could be controlled by the wearer, by another person, or through automatised means, either directly on the hearing aid or other device worn at the ear level or at a distance (e.g., requested by the parent through a mobile device 48, 48' application for a toddler in day-care, with the option to 'export' the controlling and monitoring possibilities for a given period of time to another mobile device 48, 48' such as the grandparents' mobile device 48, 48').

Most applications would be digital, but some low-cost applications could be analogue (e.g., printed pigments as a chemical sensor for bacteria). For all applications, an automated system could store levels for display of trends over time ("self-monitoring"), with the option to send the information to third parties such as health professionals 46, electronic health records, or social media. The automated system should also be able to detect levels outside the normal range (normal range level should be individualised, e.g. abnormal body temperature should be age-dependent). Detection of abnormal levels should trigger automated actions which would be specified by the wearer 8, 8' or by another person.

The hearing devices 8, 8' may be configured to detect pulse and blood pressure levels and inform a health professional 46 via a smartphone 48, 48' in case that the detected levels are within a predefined critical range.

The hearing devices 8, 8' may be configured to detect an abnormal stress level in difficult listening environments triggered by an increased digital signal processing activity in a hearing device 8, 8'.

The hearing devices 8, 8' may be configured to detect the sugar levels and inform a health professional 46 via a smartphone 48, 48' in case that the detected levels are within a predefined critical range. The hearing device user may be informed that an insulin dose is required.

A parent to a child 20, 20' wearing a hearing device 8, 8' may call a health professional 46 to find out if medication is required in case the child 20, 20' is sick. Since the hearing device 8, 8' is provided with a sensor (not shown), the hearing device 8, 8' is capable of conducting a measurement, e.g. of the body temperature of the child 20, 20'. Accordingly, the hearing device 8, 8' detects the body temperature of the child 20, 20' and sends the information to a health professional 46. The information may be sent via wireless data connections 14, 16, 16' and the Internet 12 by using a sending smartphone 48 and a receiving smartphone 48' as indicated in FIG. 10.

The temperature measurement may be conducted automatically on a regular basis (such as once every quarter of an hour or every hour) or on demand. The hearing device 8, 8' may be configured to receive an "instruction" to conduct a measurement initiated by the health professional 46 by means of his smartphone 48'. The smartphone 48' of the health professional 46 may e.g. display a text indicating the temperature, resting heart rate of the hearing device user 20, 20'. Accordingly, the health professional 46 is capable of remotely treating the hearing device user 20, 20' on the basis of the measurements taken by the hearing devices 8, 8'.

The smartphones 48, 48' may be replaces by other electronic devices (e.g. a computer or a tablet) comprising a suitable communication unit.

In an aspect, the functions may be stored on or encoded as one or more instructions or code on a tangible computer-readable medium. The computer readable medium includes computer storage media adapted to store a computer program comprising program codes, which when running on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A monitoring system for monitoring parameters of hearing devices, wherein the monitoring system comprises
a central unit configured to communicate with an internet and/or cloud service;
a plurality of hearing devices worn by a plurality of users, each of said hearing devices having
one or more sensors configured to perform measurements from said hearing device, and
memory configured to
store a set of measurement parameters based on said measurements, and
store a set of performance parameters of said hearing device,
wherein each of said hearing devices is configured to transmit said stored performance and/or measurement parameters through a wireless signal;
said monitoring system furthermore comprising
a number of access points configured to receive said transmitted stored performance and/or measurement parameters through said wireless signal transmitted by each of said plurality of hearing devices,
wherein said number of access points furthermore are configured to transmit said received performance and/or measurement parameters to said central unit, wherein said number of access points have a mesh configuration and are communicatively connected to one other, to said plurality of hearing devices, and to said central unit via a wireless personal area network such that
each of said number of access points is configured to communicate via said personal area network with at least one other access point of said monitoring system, and with any of said plurality of hearing devices within a predefined range, and
said performance and/or measurement parameters transmitted by each of said plurality of hearing devices is relayed to said central unit through a combination of said one or more access points dependent on the corresponding user's location relative to said number of access points;
said central unit comprising
a processing unit having a set of stored normal values representing each of said one or more measurements and/or performance parameters for each of said plurality of users, and
said processing unit being configured to evaluate said received performance and/or measurements parameters relayed from each of said plurality of hearing devices against said set of stored normal values for the corresponding one of said plurality of users, in order to detect a deviation from said normal value, wherein when a deviation is detected said processing unit triggers said central unit to prompt an alarm to a supervisory user of said monitoring system and/or to transmit a notification signal directly to said hearing device via said personal wireless network.

2. A monitoring system according to claim 1, wherein said transmitted performance and/or measurements parameters are communicated to said central unit through at least two access points.

3. A monitoring system according to claim 1, wherein said transmitted performance and/or measurement parameters comprises an identification parameter, wherein said central unit is configured to receive said identification parameter and correlate said received identification parameter with a set of identification parameters stored in said central unit, so as to identify the hearing device of said transmitted parameters.

4. A monitoring system according to claim 1, wherein the number of access points is configured to request a status from one or more hearing devices, said request being made periodically and/or in response to instructions transmitted from said central unit.

5. A monitoring system according to claim 1, wherein the hearing devices continuously transmits performance and/or measurement parameters to said access points, wherein said access point is configured to store said performance and/or measurement parameter, such that upon request from said central unit, said performance and/or measurement parameters are transmitted to said central unit.

6. A monitoring system according to claim 1, wherein said central unit is communicatively connected to an internet and/or cloud service, wherein said cloud is configured to store said performance and/or measurement parameters transmitted to said central unit through said access points, wherein said internet and/or cloud service is configured to transmit said measurement and/or performance data to a remote location of said location of said central unit.

7. A monitoring system according to claim 1, wherein said measurement parameters transmitted by said one or more hearing devices includes stored measurements of:
a blood sugar value, and/or
a heart rate and/or a temperature and/or
an acceleration and/or
a vibration and/or
a blood pressure and/or
a skin conductance and/or
an ultraviolet light exposure and/or
a pH level and/or
a bacteria level and/or
a humidity and/or
an electrical activity of the brain of the hearing device user(s) and/or
wherein said performance parameters includes a registration of:
a battery status of the hearing devices and/or
a surroundings and/or a positioning.

8. A monitoring system according to claim 1, wherein the control unit of said monitoring system upon a detected deviation in said transmitted one or more parameters of said one or more hearing device is configured to automatically notify an external device.

9. A monitoring system according to claim 1, wherein the monitoring system is configured as a service platform configured to be installed in a care center environment, wherein said performance and/or measurement parameters may be monitored for said plurality of hearing devices at the same time through said central unit in a structured manner.

10. A monitoring system according to claim 1, wherein said number of access points are configured as a plurality of communication devices comprising a battery electrically connected to a printed circuit board having an integrated transmitter unit comprising a radio unit and an antenna for transmission of wireless radio signals, and wherein said plurality of communication devices are installed in a common facility.

11. A monitoring system according to claim 1, wherein the monitoring system is configured to send one or more notifications to one or more of the hearing device users.

12. A monitoring system according to claim 1, wherein the one or more access points comprises a memory for storing the transmitted performance and/or measurement parameters.

13. A monitoring system according to claim 1, wherein the one or more sensors are arranged at least in connection with the hearing devices and/or are in communication with one or more sensors placed on a body part of a user.

14. A monitoring system according to claim 1, wherein a signal transmitter is arranged in connection with a first hearing device of a particular user, and a signal sensor is arranged in connection with a second hearing device of the particular user, wherein said signal transmitter is configured to transmit a signal to said signal sensor and said signal sensor is configured to receive a signal from said signal transmitter to measure magnetic and/or electric conductance in the particular user's head.

15. A monitoring system according to claim 2, wherein said transmitted performance and/or measurement parameters comprises an identification parameter, wherein said central unit is configured to receive said identification parameter and correlate said received identification parameter with a set of identification parameters stored in said central unit, so as to identify the hearing device of said transmitted parameters.

16. A monitoring system according to claim 2, wherein the number of access points is configured to request a status from one or more hearing devices, said request being made periodically and/or in response to instructions transmitted from said central unit.

17. A monitoring system according to claim 3, wherein the number of access points is configured to request a status from one or more hearing devices, said request being made continuously and/or in response to instructions transmitted from said central unit.

18. A monitoring system according to claim 2, wherein the hearing devices continuously transmits performance and/or measurement parameters to said access points, wherein said access point is configured to store said performance and/or measurement parameter, such that upon request from said central unit, said performance and/or measurement parameters are transmitted to said central unit.

19. A monitoring system according to claim 3, wherein the hearing devices continuously transmits performance and/or measurement parameters to said access points, wherein said access point is configured to store said performance and/or measurement parameter, such that upon request from said central unit, said performance and/or measurement parameters are transmitted to said central unit.

20. A monitoring system according to claim 4, wherein the hearing devices continuously transmits performance and/or measurement parameters to said access points, wherein said access point is configured to store said performance and/or measurement parameter, such that upon request from said central unit, said performance and/or measurement parameters are transmitted to said central unit.

21. A monitoring system according to claim 1, wherein at least one of the access points is a smartphone.

* * * * *